(12) United States Patent
Bradley et al.

(10) Patent No.: US 9,081,017 B2
(45) Date of Patent: Jul. 14, 2015

(54) METHODS FOR IDENTIFYING MODULATORS OF TUMOR NECROSIS FACTOR RECEPTORS

(75) Inventors: John Bradley, Cambridge (GB); Jordan Pober, New Haven, CT (US); Paul Clark, New Haven, CT (US); Wang Min, New Haven, CT (US); Martin Kluger, New Haven, CT (US)

(73) Assignees: Cambridge Enterprise Limited, Cambridge (GB); Yale University, New Haven, CT (US)

( * ) Notice: Subject to any disclaimer, the term of this patent is extended or adjusted under 35 U.S.C. 154(b) by 1692 days.

(21) Appl. No.: 11/911,177

(22) PCT Filed: Apr. 11, 2006

(86) PCT No.: PCT/GB2006/001313
§ 371 (c)(1),
(2), (4) Date: Oct. 10, 2007

(87) PCT Pub. No.: WO2006/109044
PCT Pub. Date: Oct. 19, 2006

(65) Prior Publication Data
US 2008/0176796 A1    Jul. 24, 2008

Related U.S. Application Data

(60) Provisional application No. 60/762,596, filed on Jan. 27, 2006.

(30) Foreign Application Priority Data

Apr. 11, 2005 (GB) .................................. 0507289.7

(51) Int. Cl.
| | |
|---|---|
| G01N 33/53 | (2006.01) |
| G01N 33/566 | (2006.01) |
| C07K 14/715 | (2006.01) |
| C07K 16/28 | (2006.01) |
| A61K 39/395 | (2006.01) |
| G01N 33/68 | (2006.01) |
| A61K 38/19 | (2006.01) |

(52) U.S. Cl.
CPC .......... *G01N 33/6863* (2013.01); *A61K 38/191* (2013.01); *G01N 2333/715* (2013.01); *G01N 2500/04* (2013.01); *G01N 2800/32* (2013.01); *G01N 2800/347* (2013.01)

(58) Field of Classification Search
CPC ............ A61K 38/161; G01N 33/6863; G01N 2500/04; G01N 2800/32; G01N 2333/7151
See application file for complete search history.

(56) References Cited

U.S. PATENT DOCUMENTS

| | | | |
|---|---|---|---|
| 2002/0131959 A1 | 9/2002 | Buschmann | |
| 2003/0120043 A1* | 6/2003 | Goeddel et al. | 530/351 |
| 2006/0002935 A1* | 1/2006 | Brewis et al. | 424/145.1 |

FOREIGN PATENT DOCUMENTS

| | | |
|---|---|---|
| WO | 00/56405 | 9/2000 |
| WO | 01/47533 | 7/2001 |
| WO | WO 01/47533 A * | 7/2001 |

OTHER PUBLICATIONS

Tobiume K., et al. Activation of apoptosis signal-regulating kinase 1 by the stress-induced activating phosphorylation of pre-formed oligomer. Journal of Cellular Physiology, 2002, vol. 191, p. 95-104.*
Vandenabeele P. et al. Two tumor necrosis factor receptors: structure and function. Trends in Cell Biology, 1995, vol. 5, p. 392-399.*
Zhang R., et al. Ekt/Bmx transactivates vascular enothelial growth factor 2 and recruits phosphatidylinositol 3-kinase to mediate the tumor necrosis factor-induced angiogenic pathway. Journal of Biological Chemistry, 2003, vol. 278, No. 51, p. 51267-51276.*
Higuchi Y, et al. Tumor necrosis factor receptors 1 and 2 differentially regulate survival, cardiac dysfunction, and remodeling in transgenic mice with tumor necrosis factor-alpha-induced cardiomyopathy. Circulation, 2004, vol. 109, p. 1892-1897.*
Guo G, et al. Role of TNFR1 and TNFR2 receptor in tubulointerstitial fibrosis of obstructive nephropathy. Am. J. Physiol., 1999, vol. 277, p. F766-F772.*
Vielhauer V, et al. Renal cell-expressed TNF receptor 2, not receptor 1, is essential for the development of glomerulonephritis. J. Clin. Invest., 2005, vol. 115, p. 1199-1209.*
Ramani R, et al. Inhibition of tumor necrosis factor receptor-1-mediated pathways has beneficial effects in a murine model of postischemic remodeling. Am. J. Physiol., 2004, vol. 287, p. H1369-H1377.*

(Continued)

*Primary Examiner* — Robert Landsman
*Assistant Examiner* — Bruce D Hissong
(74) *Attorney, Agent, or Firm* — Klarquist Sparkman, LLP

(57) ABSTRACT

This invention relates to the identification and characterization of specific cellular responses which are associated with tumor necrosis factor receptor 1 (TNFR1) and tumor necrosis factor receptor 1 (TNFR2). Selective modulation of these tumor necrosis factor receptors (TNFRs) Selective modulations of these responses may be useful in the promotion or inhibition of cell growth, for example, in the treatment of disease conditions, including cardiovascular and kidney diseases. Therapeutic methods employed selective TNFR1 and TNFR2 modulators are provided, along with screening methods for the identification of selective TNFR1 and TNFR2 modulators useful in such methods.

12 Claims, 18 Drawing Sheets

(56) References Cited

OTHER PUBLICATIONS

Zhang H, et al. AIP1/DAB2IP, a novel member of the Ras-GAP family, transduces TRAF2-induced ASK1-JNK activation. J. Biol. Chem., 2004, vol. 279, p. 44955-44965.*

Al-Lamki et al., "TNFR1-and TNFR2 mediated signaling pathways in human kidney are cell type-specific and differentially contribute to renal injury," *FASEB Journal* 19(12): 1637-1645, 2005.

Al-Lamki et al., "Expression of tumor necrosis factor receptors in normal kidney and rejecting renal transplants," *Laboratory Investigation* 81(11): 1503-1515, 2001.

Ostade et al., "Human tumor necrosis factor mutants with preferential binding to and activity on either the R55 or R15 receptor," *European Journal of Biochemistry* 3(220): 771-779, 1994.

Vickers et al., "Efficient reduction of target RNAs by small interfering RNA and RNase H-dependent antisense agents: a comparative analysis," *Journal of Biological Chemistry* 278(9): 7108-7118, 2003.

* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: siRNA molecule ISIS121736

<400> SEQUENCE: 1
ggtggccttc agcaggagct                                                    20

<210> SEQ ID NO 2
<211> LENGTH: 42
<212> TYPE: PRT
<213> ORGANISM: Homo sapiens

<400> SEQUENCE: 2

Gln Val Pro Phe Ser Lys Glu Glu Cys Ala Phe Arg Ser Gln Leu Glu
1               5                   10                  15

Thr Pro Glu Thr Leu Leu Gly Ser Thr Glu Glu Lys Pro Leu Pro Leu
            20                  25                  30

Gly Val Pro Asp Ala Gly Met Lys Pro Ser
        35                  40
```

METHODS FOR IDENTIFYING MODULATORS OF TUMOR NECROSIS FACTOR RECEPTORS

CROSS REFERENCE TO RELATED APPLICATIONS

This is the U.S. National Stage of International Application No. PCT/GB2006/001313, filed Apr. 11, 2006, which was published in English under PCT Article 21(2), and which in turn claims the benefit of U.S. Provisional Application No. 60/762,596, filed Jan. 26, 2006 and of Great Britain Application No. 0507289.7, filed Apr. 11, 2005. All three applications are incorporated herein in their entirety.

This invention relates to the assessment and treatment of disease conditions, including renal and cardiovascular disease, by the selective modulation of tumour necrosis factor receptors (TNFRs).

The importance of tumour necrosis factor (TNF; also known as TNFα) in human disease has been highlighted by the efficacy of anti-TNF antibodies or soluble TNF receptors (TNFRs) in controlling disease activity in rheumatoid arthritis and other inflammatory conditions. TNF interacts with two distinct receptors, designated TNFR1 and TNFR2, and understanding the specific role of each receptor in TNF signalling is important for rational use of TNF blockade. The signalling events initiated by each TNFR vary among cell types in culture and little is known about TNFR signalling in situ in different tissues.

The cytoplasmic sequences of TNFR1 and TNFR2 share no homology and both are devoid of intrinsic enzyme activity. Instead, TNFR1 and TNFR2 initiate signalling by recruitment of cytosolic proteins through protein-protein interaction domains in their cytoplasmic regions. TNFR1 signals by recruitment to its death domain of TNFR-associated-death-domain protein (TRADD) (Jones, S. J et al. (1999) *J. Immunol.* 162:1042-1048), which serves as a supporting structure for recruitment of TNF-receptor associated factor 2 (TRAF2) and receptor-interacting protein-1 (RIP-1). The signalling complex, which is formed leads to activation of transcription factors such as NFκB and AP-1. TNFR2 does not contain a cytoplasmic death domain although it can interact directly with TRAF2 (Rothe, M. et al (1994) *Cell* 78:681-692), providing a mechanism for some shared activity of TNFRs.

TNFR1 and TNFR2 differentially activate Apoptosis signalling kinase-1 (ASK1) and endothelial/epithelial tyrosine kinase (Etk) (FIG. 1). ASK1 is a kinase which is activated by TNF through TNFR1 and activates multiple pro-apoptotic pathways in cultured cells. ASK1 activity is controlled by several mechanisms, including protein-protein interactions with thioredoxin (Trx), the dimeric phosphoserine-binding molecule 14-3-3, and TRAF2. ASK1 activation can be assessed by loss of phosphorylation at Ser 967 coupled with de novo phosphorylation at Thr845.

Etk (also known as Bmx; bone marrow tyrosine kinase in chromosome X) or is a kinase which is activated by TNF through TNFR2 and has been implicated in cell adhesion, migration, proliferation, and survival (Tamagnone, L. et al (1994) *Oncogene* 9:3683-3688, Abassi, Y. A. et al (2003) *J. Biol. Chem.* 278:35636-35643). In epithelial cells, Etk may be a regulator of cell junctions (Hamm-Alvarez, S. F. et al. (2001) *Am. J. Physiol Cell Physiol* 280:C1657-C1668). In vascular endothelial cells (EC), Etk is involved in TNF-induced angiogenic events (Zhang, R. et al (2003) *J. Clin. Invest* 111:1933-1943, Pan, S. et al (2002) *Mol. Cell Biol.* 22:7512-7523) and mediates activation of the phosphatidylinositol 3 kinase (PI3K)-Atk angiogenic pathway, which is involved in growth factor stimulated cell migration (Kureishi, Y. et al (2000) *Nat. Med.* 6:1004-1010) The appearance and phosphorylation of Etk in EC is indicative of TNFR2 signalling.

The present inventors have exploited the TNFR-specific recruitment and activation of ASK1 and Etk to identify specific cellular responses which are associated with TNFR1 and TNFR2. Manipulation of these responses may be useful in the treatment of disease conditions, in particular vascular and kidney diseases and disease conditions associated with inflammation or ischaemia.

One aspect of the invention provides a selective TNFR2 agonist for use in the treatment of a disease condition or the use of a selective TNFR2 agonist in the manufacture of a medicament for use in the treatment of disease condition.

A related aspect of the invention provides a method of treating a disease condition in an individual comprising:

administering a selective TNFR2 agonist to said individual

A selective TNFR2 agonist stimulates TNFR2 signalling but has little or no effect on TNFR1 signalling. For example, the selective TNFR2 agonist may promote Etk expression and/or phosphorylation without promoting ASK Thr845 phosphorylation. In some embodiments, a selective TNFR2 agonist may bind to TNFR2 and show little or no binding to TNFR1.

Selective TNFR2 agonists include TNF polypeptides which bind preferentially to TNFR2 relative to TNFR1. The structure and activity of TNF has been well-characterised in the art. The residues involved in TNF receptor binding are located at the base of the homotrimeric structure of TNF at each side of the intersubunit groove that separates two monomeric TNF subunits (Van Ostade X et al (1991) *EMBO J.* April 10(4): 827-36). Mutation of these receptor-binding residues may confer specificity for TNFR2 and the skilled person is readily able to produce and characterise suitable TNF polypeptides with specificity for TNFR2 relative to TNFR1.

A suitable TNF polypeptide which binds bind preferentially to TNFR2 relative to TNFR1 may comprise or consist of the wild-type TNF alpha sequence (NP_000585.2 GI: 25952111) or a variant thereof, with one or more mutations which increase TNFR2 binding relative to TNFR1 binding or, conversely, reduce TNFR1 binding relative to TNFR2 binding. Suitable mutations include non-conservative substitutions of the Asp residue at position 143, including for example, Asp143Tyr, Asp143Phe, or Asp143Asn (Van Ostade X et al. (1994) Eur J Biochem. March 15; 220(3): 771-9). A TNF polypeptide may further include non-conservative substitutions of the Ala residue at position 145, for example Ala145Arg.

Selective TNFR2 agonists may also include antibodies or fragments thereof which specifically bind to TNFR2 and stimulate TNFR2 signalling. Suitable antibodies bind preferentially to TNFR2 relative to TNFR1 and may show little or no binding to TNFR1.

An antibody that specifically binds to TNFR2 and stimulates TNFR2 mediated TNF signalling may be generated using techniques which are conventional in the art. Methods of producing antibodies include immunising a mammal (e.g. mouse, rat, rabbit, horse, goat, sheep or monkey) with a target polypeptide or a peptide fragment of the target. Antibodies may be obtained from immunised animals using any of a variety of techniques known in the art, and screened, preferably using binding of antibody to antigen of interest. For instance, Western blotting techniques or immunoprecipitation may be used (Armitage et al., (1992) Nature 357, 80-82).

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies or fragments identified as displaying specific binding to TNFR2 may be tested for ability to stimulate TNFR2 mediated TNF signalling using the techniques described herein.

Another aspect of the invention provides a selective TNFR1 antagonist for use in treatment of a disease condition and the use of a selective TNFR1 antagonist in the manufacture of a medicament for use in the treatment of a disease condition.

A related aspect of the invention provides a method of treating a disease condition in an individual comprising:
administering a selective TNFR1 antagonist to said individual.

A selective TNFR1 antagonist is a molecule which preferentially inhibits the binding of TNF to TNFR1 relative to TNFR2. For example a selective TNFR1 antagonist may reduce or block the binding of TNF to TNFR1 whilst having little or no effect on the binding of TNF to TNFR2. A selective TNFR1 antagonist may allow the stimulation of TNFR2 signalling by TNF but will reduce or prevent the stimulation of TNFR1 signalling by TNF. For example, the selective TNFR1 antagonist may inhibit or prevent the stimulation of ASK Thr845 phosphorylation in the presence of TNF but may allow the stimulation of Etk expression and/or phosphorylation.

Examples of selective TNFR1 antagonists include antibodies or fragments thereof which bind to TNFR1 but do not bind to TNFR2. Suitable antibodies inhibit or block the binding of TNF to TNFR1 but do not themselves stimulate TNFR1 mediated TNF signalling. Methods for producing suitable antibodies are well known in the art and are described in more detail above.

Selective modulation of TNFR1 and TNFR2 may be useful in the treatment of a range of disease conditions, including kidney disorders and cardiovascular disorders in particular disease conditions associated with or characterised by cell damage or cell death.

TNFR2 agonists and/or TNFR1 antagonists are shown herein to promote cell growth and may be important in the regeneration and repair of damaged tissues, for example, tissue damaged by ischaemia or inflammation. For example, TNFR2 agonists and/or TNFR1 antagonists may be useful in tubular repair and regeneration in the kidney following acute transplant rejection or acute tubular necrosis and in the treatment of cardiovascular disorders such as coronary heart disease (CHD) and coronary artery disease, cardiomyopathy and cardiac allograft rejection and non-cardiac vascular disorders such as peripheral vascular/arterial disease.

One aspect of the invention provides a selective TNFR1 agonist for use in the treatment of a disease condition or the use of a selective TNFR1 agonist in the manufacture of a medicament for use in the treatment of disease condition.

A related aspect of the invention provides a method of treating a disease condition in an individual comprising:
administering a selective TNFR1 agonist to an individual in need thereof.

A selective TNFR1 agonist stimulates TNFR1 signalling but has little or no effect on TNFR2 signalling. For example, the selective TNFR1 agonist may promote ASK Thr845 phosphorylation without promoting Etk expression and/or phosphorylation. In some embodiments, a selective TNFR1 agonist may bind to TNFR1 and show little or no binding to TNFR2.

Selective TNFR1 agonists include TNF polypeptides which bind preferentially to TNFR1 relative to TNFR2. As described above, the skilled person is readily able to produce and characterise suitable TNF polypeptides with specificity for TNFR1 relative to TNFR2. A suitable TNF polypeptide which binds bind preferentially to TNFR2 relative to TNFR1 may comprise or consist of the wild-type TNF alpha sequence (NP_000585.2 GI: 25952111) or a variant thereof, with one or more mutations which increase TNFR1 binding relative to TNFR2 binding or, conversely, reduce TNFR2 binding relative to TNFR1 binding. Suitable mutations include non-conservative substitutions of the arginine residue at position 32, including for example, Arg32Trp (Van Ostade X et al. (1994) Eur J Biochem. March 15; 220(3):771-9). A TNF polypeptide may further include non-conservative substitutions of the Ser residue at position 86, for example Ser86Thr.

Selective TNFR1 agonists may also include antibodies or fragments thereof which specifically bind to TNFR1 and stimulate TNFR1 signalling. Suitable antibodies bind preferentially to TNFR1 relative to TNFR2 and may show little or no binding to TNFR2. An antibody that specifically binds to TNFR1 and stimulates TNFR1 mediated TNF signalling may be generated using techniques which are described in more detail above.

Another aspect of the invention provides a selective TNFR2 antagonist for use in treatment of a disease condition and the use of a selective TNFR2 antagonist in the manufacture of a medicament for use in the treatment of a disease condition.

A related aspect of the invention provides a method of treating a disease condition in an individual comprising:
administering a selective TNFR2 antagonist to said individual.

A selective TNFR2 antagonist is a molecule which preferentially inhibits the binding of TNF to TNFR2 relative to TNFR1. For example a selective TNFR2 antagonist may reduce or block the binding of TNF to TNFR2 whilst having little or no effect on the binding of TNF to TNFR1. A selective TNFR2 antagonist may allow the stimulation of TNFR1 signalling by TNF but will reduce or prevent the stimulation of TNFR2 signalling by TNF. For example, the selective TNFR2 antagonist may inhibit or prevent the stimulation of Etk expression and/or phosphorylation in the presence of TNF but may allow the stimulation of ASK Thr845 phosphorylation.

Examples of selective TNFR2 antagonists include antibodies or fragments thereof which bind to TNFR2 but do not bind to TNFR1. Suitable antibodies inhibit or block the binding of TNF to TNFR2 but do not themselves stimulate TNFR2 mediated TNF signalling. Methods for producing suitable antibodies are well known in the art and are described in more detail above Selective modulation of TNFR1 and TNFR2 may be useful in the treatment of a range of disease conditions, including kidney disorders and cardiovascular disorders, in particular disease conditions associated with or characterised by cellular proliferation.

TNFR1 agonists and/or TNFR2 antagonists may be useful in preventing cell growth and proliferation, for example in the treatment of proliferative conditions. Proliferative conditions may include conditions which include or are characterised by the development of an inflammatory response which involves proliferation of inflammatory cells. For example, TNFR1 agonists and/or TNFR2 antagonists may be useful in preventing the cellular proliferation which occurs in glomerular cells in glomerulonephritis, and the proliferation of mesangial cells and leucocyte proliferation, which occurs in vasculitis, such as renal vasculitis. TNFR1 agonists and/or TNFR2 antagonists may also be useful in the treatment of cancers, in particular kidney cancers such as renal cell carcinoma.

In some preferred embodiments, a TNFR1 or TNFR2 antagonist may selectively down-regulate the expression of TNFR1 or TNFR2, respectively. This may be used in the treatment of a disease condition as described above. Down regulation may occur, for example, through RNA interference (RNAi).

Small RNA molecules may be employed to regulate gene expression. These include targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

A role for the RNAi machinery and small RNAs in targeting of heterochromatin complexes and epigenetic gene silencing at specific chromosomal loci has also been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 19-nt or 20-nt siRNA is generally long enough to induce gene-specific silencing, but short enough to evade host response. The decrease in expression of targeted gene products can be extensive with 90% silencing induced by a few molecules of siRNA.

In the art, these RNA sequences are termed "short or small interfering RNAs" (siRNAs) or "microRNAs" (miRNAs) depending in their origin. Both types of sequence may be used to down-regulate gene expression by binding to complimentary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

Accordingly, the present invention provides the use of these sequences as TNFR1 or TNFR2 antagonists for down-regulating the expression of TNFR1 or TNFR2, respectively.

The siRNA ligands are typically double stranded and, in order to optimise the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed on John et al, PLOS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design of suitable siRNA and miRNA sequences, for example using resources such as Ambion's siRNA finder, available on the World Wide Web at www.ambion.com/techlib/misc/siRNA_finder.html. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) *Nature Biotechnology* 21:324-328). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell.

Preferably, the shRNA molecule comprises a partial sequence of TNFR1 or TNFR2 mRNA. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of TNFR1 or TNFR2 mRNA.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific promoter. In a further embodiment, the siRNA, longer dsRNA or miRNA is produced exogenously (in vitro) by transcription from a vector.

In one embodiment, the vector may comprise a nucleic acid sequence according to the invention in both the sense and antisense orientation, such that when expressed as RNA the sense and antisense sections will associate to form a double stranded RNA. Preferably, the vector comprises TNFR1 or TNFR2 nucleic acid sequences; or variants or fragments thereof. In another embodiment, the sense and antisense sequences are provided on different vectors.

Alternatively, siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through-O-or-S—.

Methods relating to the use of RNAi to silence genes in *C. elegans*, *Drosophila*, plants, and mammals are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619, and Elbashir S M, et al., 2001 Nature 411:494-498).

Suitable RNAi molecules for down-regulation of TNFR1 or TNFR2 may possible 85% or more, 90% or more, 95% or more or 100% sequence identity with a contiguous sequence of 10 to 40 nucleotides from the TNFR1 or TNFR2 mRNA sequence.

Suitable RNAi molecules for down-regulation of TNFR1 include the molecule GGTGGCCTTCAGCAGGAGCT (termed ISIS121736; SEQ ID NO: 1) which is described in Vickers et al (2003) JBC 278 7108.

A method of identifying and/or obtaining a compound useful in therapy may comprise;
  contacting a test compound with a cell which expresses a TNFR1 polypeptide and a TNFR2 polypeptide, and;
  determining the expression of said TNFR1 and TNFR2 polypeptide in the presence of the test compound.

A reduction in the expression of the TNFR1 polypeptide relative to the expression of the TNFR2 polypeptide may be indicative that the compound is a cell growth promoter and a reduction in the expression of the TNFR2 polypeptide relative to the expression of the TNFR1 polypeptide may be indicative that the compound is a cell growth inhibitor.

Suitable test compounds include sense or anti-sense TNFR1 or TNFR2 nucleic acid, for example an RNAi, siRNA, longer dsRNA, shRNA or miRNA molecule as described above. In some embodiments, the test compound may comprise 15-25 contiguous nucleotides from the mRNA sequence of TNFR1 or TNFR2, or the complement thereof.

Other aspects of the invention relate to methods of identifying and/or obtaining compounds, such as selective TNFR2 agonists or TNFR1 antagonists, which are useful in treating disease conditions as described herein.

A method of identifying and/or obtaining a compound useful in treating a disease condition may comprise,
  contacting a test compound with a TNFR1 polypeptide and a TNFR2 polypeptide, and;
  determining the interaction of the compound with said polypeptides.

In some embodiments, interaction of the compound may be determined by determining binding. A test compound which binds preferentially to the TNFR1 polypeptide relative to the TNFR2 polypeptide or vice versa may be investigated further, for example by determining the relative activation of the TNFR2 and TNFR1 polypeptides by the test compound.

In some embodiments, interaction of the compound may be determined by determining the relative activation of the TNFR1 and TNFR2 polypeptides by the test compound.

Preferential activation of the TNFR2 polypeptide relative to the TNFR1 polypeptide may be indicative that the test compound is a selective TNFR2 agonist that is useful in promoting cell growth, for example in the treatment of a disease condition as described above. Preferential activation of the TNFR1 polypeptide relative to the TNFR2 polypeptide may be indicative that the test compound is a selective TNFR1 agonist that is useful in inhibiting cell growth and proliferation, for example in the treatment of a disease condition as described above.

Preferential binding to the TNFR1 polypeptide relative to the TNFR2 polypeptide, without activation of the TNFR1 polypeptide may be indicative that the test compound is a selective TNFR1 antagonist which may be useful in promoting cell growth, for example in the treatment of a disease condition as described above. Such a compound may be tested further to determine its effect on the binding of TNF to TNFR1 as described below.

Preferential binding to the TNFR2 polypeptide relative to the TNFR'1 polypeptide, without activation of the TNFR2 polypeptide may be indicative that the test compound is a selective TNFR2 antagonist which may be useful in inhibiting cell growth and proliferation, for example in the treatment of a disease condition as described above. Such a compound may be tested further to determine its effect on the binding of TNF to TNFR2 as described below.

Activation of a TNFR1 polypeptide includes an increase in TNF signalling activity through the TNFR1 polypeptide and may be determined by any convenient method. Suitable methods include, for example, determining the phosphorylation of ASK1 at residue Tyr 845 and/or the absence of phoshorylation at residue Ser 966, determining the up-regulation of E-selectin in endothelial cells (Slowik M R et al. Am J Pathol. (1993) 143(6): 1724-30) and determining the apoptosis of cells, for example kidney cells, expressing the TNFR1 polypeptide.

Activation of TNFR2 polypeptide includes an increase in TNF signalling activity through the TNFR2 polypeptide and may be determined by any convenient method, for example by determining the level and/or phosphorylation of Etk. In some embodiments, activation may be determined by determining the proliferation of cells, for example kidney cells, expressing the TNFR2 polypeptide.

A method of identifying and/or obtaining a compound useful in treating a disease condition,
  determining the interaction between a TNFR1 polypeptide and a TNF polypeptide in the presence of a test compound; and,
  determining the interaction between a TNFR2 polypeptide and a TNF polypeptide in the presence of said test compound.

A reduction in the interaction of TNF polypeptide with the TNFR1 polypeptide relative to the TNFR2 polypeptide in the presence of the test compound may be indicative that the compound is a selective TNFR1 antagonist which is useful in promoting the growth and proliferation of cells and may therefore be useful in treating disease conditions as described above.

A reduction in the interaction of TNF polypeptide with the TNFR2 polypeptide relative to the TNFR1 polypeptide in the presence of the test compound may be indicative that the compound is a selective TNFR2 antagonist which is useful in inhibiting the growth and proliferation of cells and may therefore be useful in treating disease conditions as described above.

In some embodiments, the interaction of the TNFR and TNF polypeptides may be determined by detecting or measuring binding of the TNF polypeptide to the TNFR1 and TNFR2 polypeptides.

Reduced binding of the TNF polypeptide to the TNFR1 polypeptide relative to the TNFR2 polypeptide in the presence of the test compound may be indicative that the compound is useful in promoting the growth and proliferation of cells and may therefore be useful in treating a disease condition. A test compound which reduces binding of the TNF polypeptide to the TNFR1 polypeptide may be tested further, for example the effect of the test compound on the activation of the TNFR1 polypeptide may be determined. A selective TNFR1 antagonist has little or no effect on TNFR1 activation (i.e. it inhibits binding of TNF to TNFR1 but has no TNFR1 agonist activity).

Reduced binding of the TNF polypeptide to the TNFR2 polypeptide relative to the TNFR1 polypeptide in the presence of the test compound may be indicative that the compound is useful in inhibiting the growth and proliferation of cells and may therefore be useful in treating a disease condition described above. A test compound which reduces binding of the TNF polypeptide to the TNFR2 polypeptide may be tested further, for example the effect of the test compound on the activation of the TNFR2 polypeptide may be determined. A selective TNFR2 antagonist has little or no effect on TNFR2 activation (i.e. it inhibits binding of TNF to TNFR2 but has no TNFR2 agonist activity).

Polypeptides may be contacted under conditions wherein, in the absence of the test compound, the polypeptides interact or bind to each other. A TNF polypeptide may be in the reaction medium in a soluble form. TNFR1 and TNFR2 polypeptides may be in the reaction medium in a soluble form or may be comprised on a membrane.

In other embodiments, the interaction of the TNFR and TNF polypeptides may be determined by detecting or measuring the activation of the TNFR1 and TNFR2 polypeptides in the presence of the TNF polypeptide.

A test compound that allows the preferential activation by TNF of the TNFR2 polypeptide relative to the TNFR1 polypeptide (i.e. a compound that preferentially inhibits or blocks activation by TNF of the TNFR1 polypeptide relative to the TNFR2 polypeptide) may be useful in promoting cell growth, for example in the treatment of a disease condition as described herein.

A test compound that allows the preferential activation by TNF of the TNFR1 polypeptide relative to the TNFR2 polypeptide (i.e. a compound that preferentially inhibits or blocks activation by TNF of the TNFR2 polypeptide relative to the TNFR1 polypeptide) may be useful in inhibiting cell growth, for example in the treatment of a disease condition as described herein.

Activation of TNFR1 and TNFR2 polypeptides may be determined as described above.

Methods for obtaining or identifying compounds as described herein may be in vivo cell-based assays, or in vitro non-cell-based based assays. In in vitro assays, polypeptides may be isolated, fixed to a solid support or comprised on a membrane.

Suitable cell types for in vivo assays include mammalian cells such as CHO, HeLa and COS cells. The polypeptide may be heterologous to the cell (i.e. not naturally found in the cell). Those of skill in the art may vary the format of the methods described herein using routine skill and knowledge.

For example, binding between polypeptides may be determined in vitro by immobilising one polypeptide to a solid support, then bringing it into contact with the other. The binding affinity can then be determined by standard techniques, such as surface plasmon resonance. The polypeptide may be labelled with a detectable label. Suitable detectable labels include $^{35}$S-methionine, which may be incorporated into recombinantly produced peptides and polypeptides. Recombinantly produced peptides and polypeptides may also be expressed as a fusion protein containing an epitope which can be labelled with an antibody.

A method described herein may be performed in vivo, for example in a cell-line such as a yeast or mammalian cell-line in which the relevant recombinant polypeptides or peptides are expressed from one or more vectors introduced into the cell.

A TNF polypeptide for use in the present methods may have the sequence of human TNFalpha (NP_000585.2, GI:25952111) or may be a fragment or variant thereof. A TNFR1 polypeptide may have the sequence of human TNFR1 (NP_001056.1 GI:4507575) or may be a fragment or variant thereof. A TNFR2 polypeptide may have the sequence of human TNFR2 (NP_001057.1 GI:4507577) or may be a fragment or variant thereof.

Suitable variants or fragments of TNFR1 and TNFR2 polypeptides retain the activity of the wild-type sequences to interact with TNF. Suitable variants or fragments of a TNF polypeptide retain the activity of the wild-type sequence to interact with (i.e. bind and/or activate) TNFR1 and TNFR2. A variant may have one or more of addition, insertion, deletion or substitution of one or more amino acids in the wild-type polypeptide sequence. For example, up to about 5, 10, 15 or 20 amino acids may be altered. Such alterations may be caused by one or more of addition, insertion, deletion or substitution of one or more nucleotides in the encoding nucleic acid.

An amino acid sequence variant of a wild-type polypeptide sequence, may comprise an amino acid sequence which shares greater than 20% sequence identity with the wild-type sequence, greater than 30%, greater than 35%, greater than 40%, greater than 45%, greater than 55%, greater than 65%, greater than 70%, greater than about 80%, greater than 90% or greater than 95%. The sequence may share greater than 20% similarity with the wild-type sequence, greater than 30% similarity, greater than 40% similarity, greater than 50% similarity, greater than 60% similarity, greater than 70% similarity, greater than 80% similarity or greater than 90% similarity.

Sequence similarity and identity are commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used. Sequence identity and similarity may also be determined using Genomequest™ software (Gene-IT, Worcester Mass. USA).

Sequence comparisons are preferably made over the full-length of the relevant sequence described herein.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine.

Unless context dictates otherwise, determining an interaction may include detecting the interaction or measuring the level or amount of the interaction.

The amount of test substance or compound which may be employed in the methods described herein will normally be determined by trial and error depending upon the type of compound used. Typically, from about 0.001 nM to 1 mM or more concentrations of putative inhibitor compound may be used, for example from 0.01 nM to 100 µM, e.g. 0.1 to 50 µM, such as about 10 µM.

Test compounds may be natural or synthetic chemical compounds used in drug screening programmes. Extracts of plants that contain several characterised or uncharacterised components may also be used.

Combinatorial library technology (Schultz, (1996) Biotechnol. Prog. 12, 729-743) provides an efficient way of testing a potentially vast number of different substances for ability to selectively modulate TNFR activity as described herein.

One class of test compounds can be derived from the TNF, TNFR1 and/or TNFR2 polypeptide sequences. Peptide fragments of from 5 to 40 amino acids, for example, from 6 to 10 amino acids may be tested for their ability to modulate such interaction or activity. Peptides can also be generated wholly or partly by chemical synthesis according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.). Peptides may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulphonic acid or a reactive derivative thereof. The modulatory properties of a peptide may be enhanced by the addition of one of the following groups to the C terminal: chloromethyl ketone, aldehyde and boronic acid. These groups are transition state analogues for serine, cysteine and threonine proteases. The N terminus of a peptide fragment may be blocked with carbobenzyl to inhibit aminopeptidases and improve stability (Proteolytic Enzymes 2nd Ed, Edited by R. Beynon and J. Bond Oxford University Press 2001).

Antibodies directed to the TNF, TNFR1 or TNFR2 polypeptide might form a further class of putative modulator compounds. Candidate antibodies may be characterised and their binding regions determined to provide chimeric antibodies and fragments thereof which are responsible for modulating the interaction. Methods and means of producing suitable antibodies are described in more detail above.

Other candidate modulator compounds may be based on modelling the 3-dimensional structure of a polypeptide or peptide fragment and using rational drug design to provide potential inhibitor compounds with particular molecular shape, size and charge characteristics. Techniques for rational drug design are well known in the art.

Following identification of a compound using a method described above, the compound may be isolated and/or synthesised.

A compound identified using one or more primary screens (e.g. in a cell-free system) as having ability to interact with TNFR2 but not TNFR1, and/or to block the interaction of TNF with TNFR1, but not the interaction between TNF and TNFR2, may be assessed or investigated further using one or more secondary screens. Similarly, a compound identified using one or more primary screens (e.g. in a cell-free system) as having ability to interact with TNFR1 but not TNFR2, and/or to block the interaction of TNF with TNFR2, but not the interaction between TNF and TNFR1, may be assessed or investigated further using one or more secondary screens.

Biological activity, for example the induction of cell proliferation or the inhibition of cell apoptosis, may be tested in tissue culture, for example a kidney organ culture as described herein. Test compounds found to modulate the activity of TNFR2 and TNFR1 as described may be tested for activity to induce or inhibit cell growth and/or proliferation in animal models of disease conditions as described herein.

The compound may be modified to optimise its pharmaceutical properties. The modified compound may be tested using the methods described herein to see whether it has the target property, or to what extent it is exhibited. Modified compounds include mimetics of the lead compound. Further optimisation or modification can then be carried out to arrive at one or more final compounds for in vivo or clinical testing.

The test compound may be manufactured and/or used in preparation, i.e. manufacture or formulation, of a composition such as a medicament, pharmaceutical composition or drug. These may be administered to individuals, e.g. for any of the purposes discussed elsewhere herein.

A method of the invention may comprise formulating the test compound or the modified test compound in a pharmaceutical composition with a pharmaceutically acceptable excipient, vehicle or carrier as discussed further below.

Another aspect of the present invention provides a method of producing a pharmaceutical composition comprising;
 i) identifying a compound which is a selective TNFR1 antagonist or a selective TNFR2 agonist using a method described herein; and,
 ii) admixing the identified compound with a pharmaceutically acceptable carrier.

Another aspect of the present invention provides a method of producing a pharmaceutical composition comprising;
 i) identifying a compound which is a selective TNFR1 agonist or a selective TNFR2 antagonist using a method described herein; and,
 ii) admixing the identified compound with a pharmaceutically acceptable carrier.

The formulation of compositions with pharmaceutically acceptable carriers is described further below.

Another aspect of the invention provides a method for preparing a pharmaceutical composition, for example, for the treatment of a disease condition as described herein, comprising;
 i) identifying a compound which is a selective agonist of TNFR2 or a selective antagonist of TNFR1,
 ii) synthesising the identified compound, and;
 iii) incorporating the compound into a pharmaceutical composition.

Another aspect of the invention provides a method for preparing a pharmaceutical composition, for example, for the treatment of a disease condition as described herein, comprising;

i) identifying a compound which is a selective agonist of TNFR1 or a selective antagonist of TNFR2,
ii) synthesising the identified compound, and;
iii) incorporating the compound into a pharmaceutical composition.

The identified compound may be synthesised using conventional chemical synthesis methodologies. Methods for the development and optimisation of synthetic routes are well known to persons skilled in this field.

The compound may be modified and/or optimised as described above.

Incorporating the compound into a pharmaceutical composition may include admixing the synthesised compound with a pharmaceutically acceptable carrier or excipient.

Whether it is a small molecule, polypeptide, peptide, nucleic acid molecule, or other pharmaceutically useful compound that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments for the disease condition, either simultaneously or sequentially dependent upon the condition to be treated.

Pharmaceutical compositions may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Methods of the invention may also be useful in the diagnosis of a disease condition.

Another aspect of the invention provides a method of assessing a disease condition in an individual comprising;
determining in a sample obtained from said individual the activation of TNFR1 and TNFR2.

An increase in TNFR1 and/or TNFR2 activation may be indicative, for example, of a disease associated with ischaemia or inflammation, including kidney disorders such as glomerulonephritis, acute renal transplant rejection or acute tubular necrosis, a cardiovascular disorder or cancer.

A suitable sample may be a tissue sample, for example from kidney, cardiac or vascular tissue.

Activation of TNFR1 may be determined, for example, by determining the phosphorylation of apoptosis signalling kinase-1 (ASK1), in particular in endothelial cells (EC) of said sample.

Activation of TNFR2 may be determined, for example, by determining the level or phosphorylation of endothelial/epithelial tyrosine kinase (Etk), in particular in tubular epithelial cells (TEC) of the sample.

Activation of TNFR1 may be indicative of an inflammation associated disease, for example a kidney disorder such as acute rejection. Activation of TNFR2 may, for example, be indicative of acute tubular necrosis in the kidney or an associated condition.

A method of assessing the condition of a tissue may comprise:
determining in a sample obtained from said tissue one or both of the phosphorylation of ASK1 in said sample and the phosphorylation of Etk of said sample.

Phosphorylation of ASK1 may be determined at Thr845 and/or Ser967. Increased phosphorylation of Thr845 and/or decreased phosphorylation of Ser967 relative to controls may be indicative of TNFR1 activation. In some embodiments, phosphorylation of ASK1 may be determined in endothelial cells (EC) of said sample.

Phosphorylation of endothelial/epithelial tyrosine kinase (Etk) may be determined at Tyr 566. Increased phosphorylation of Tyr 566 relative to controls may be indicative of TNFR2 activation. In some embodiments, phosphorylation of Etk may be determined in tubular epithelial cells (TEC) of the sample.

Suitable tissue includes vascular, heart and kidney tissue.

The amino acid sequence of Etk has the database accession number P51813 GI: 1705489. The amino acid sequence of ASK1 has the database accession number BAA12684.1 GI: 1805500.

The level of Etk and/or the phosphorylation of ASK1 and/or Etk may be determined by standard immunological techniques. For example, the sample may be contacted with an antibody that binds specifically to the target molecule to be detected (i.e. Etk, phosphorylated Etk or phosphorylated ASK1) and the binding of the antibody to the sample determined.

An antibody which specifically binds to an antigen such as Etk, phosphorylated Etk or phosphorylated ASK1 may not show any significant binding to molecules in mammalian cells other than the antigen. An antibody that specifically binds to Etk, phosphorylated Etk or phosphorylated ASK1 may be generated using techniques which are conventional in the art as described above.

Samples to be subjected to contact with an antibody may be prepared using any available technique that allows the antibody to bind to bind to cellular polypeptides in the sample.

Binding of the antibody to the sample may be determined by any appropriate means. Tagging with individual reporter molecules is one possibility. A reporter molecule may be linked to the primary antibody that binds to the target molecule or to a secondary antibody that binds to the primary antibody. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding binding molecule (e.g. antibody) and reporter molecule. One favoured mode is by covalent linkage of a binding member with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes that catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples are horseradish peroxidase and chemiluminescence.

The mode of determining binding is not a feature of the present invention and those skilled in the art are able to choose a suitable mode according to their preference and general knowledge.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described above and tables described below.

FIG. 1 shows a model for ASK1 and Etk in kidney rejection. (A) shows TNF-α signaling pathway through TRAF2/ASK1 employing the cytokine/adaptor/MAPK paradigm. Stimulation of TNFR1 leads to recruitment of the adaptor protein TRAF2, which facilitates the release of ASK1 from its endogenous inhibitor 14-3-3. Disruption of the ASK1/14-3-3 complex and dephosphorylation of ASK1 from serine-967 (pSer967) by the unknown phosphatases results in the activation and phosphorylation of ASK1 at threonine-845 (pThr845). ASK1pThr845 in turn, activates JNK (c-Jun N-terminal kinase) leading to TNF induced cell death. (B) shows a model for Etk-mediated activation induced by TNF via TNFR2. TNF result in phosphorylation of Etk (Etkp), leading to Akt activation, which contributes to TNF-induced cell proliferation.

Figure 6:
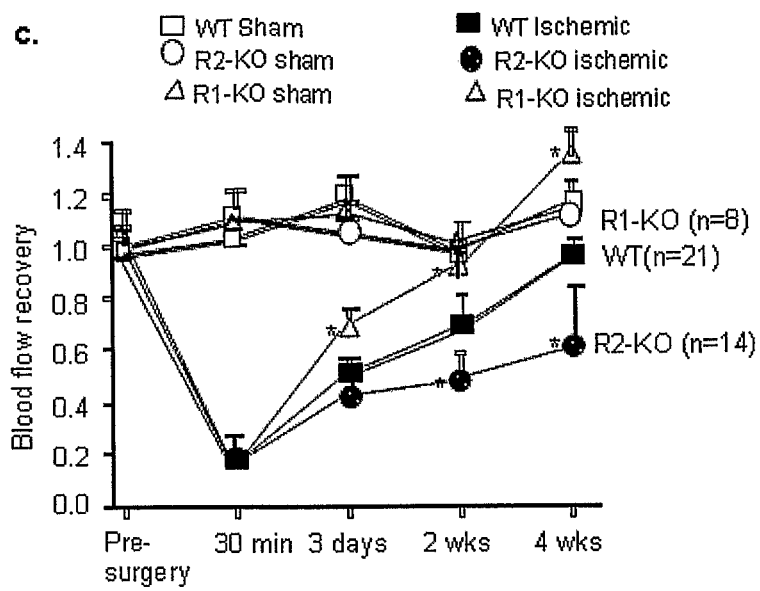

FIG. 6 shows that TNFR2-KO mice show reduced whereas TNFR1-KO mice show augmented recovery of limb perfusion compared to normal C57BL/6 mice (ratio of perfusion unit from non-ischemia (left) to ischemia (right) are shown). N number for each strain is shown in parenthesis. Data are mean±SEM, *, p<0.05.

Figure 7:
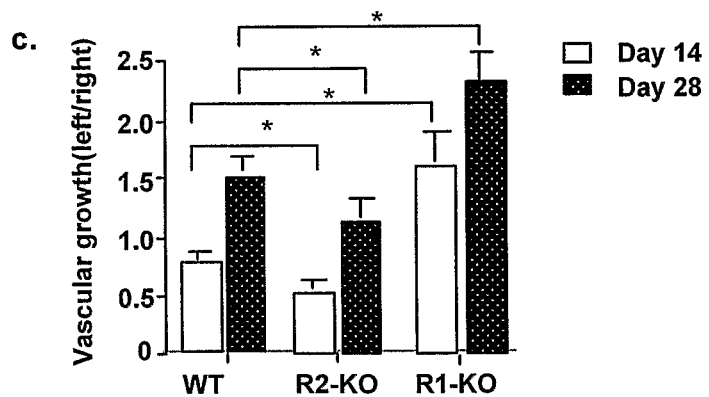

FIG. 7 shows vascular growth in the ischemic hindlimbs of TNFR2-KO compared to WT and TNFR1-KO mice after femoral ligation, quantitated as ratio of vascular density (left/right) and n=10 for each strain. *, p<0.05.

Figure 8:
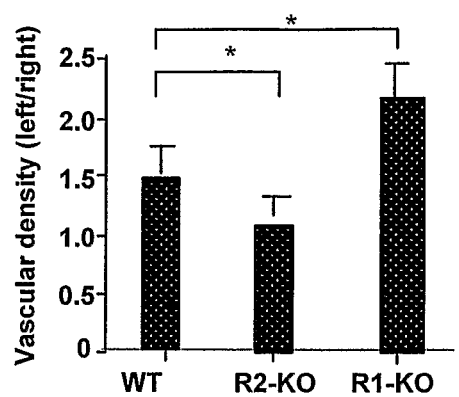

FIG. 8 shows micro-CT analyses. 4 weeks after femoral ligation, mice were subjected to postmortem infusion of barium and micro-CT and vascular growth was quantitated as ratio of vascular density (left/right) n=10 for each strain. *, p<0.05.

Figure 9:
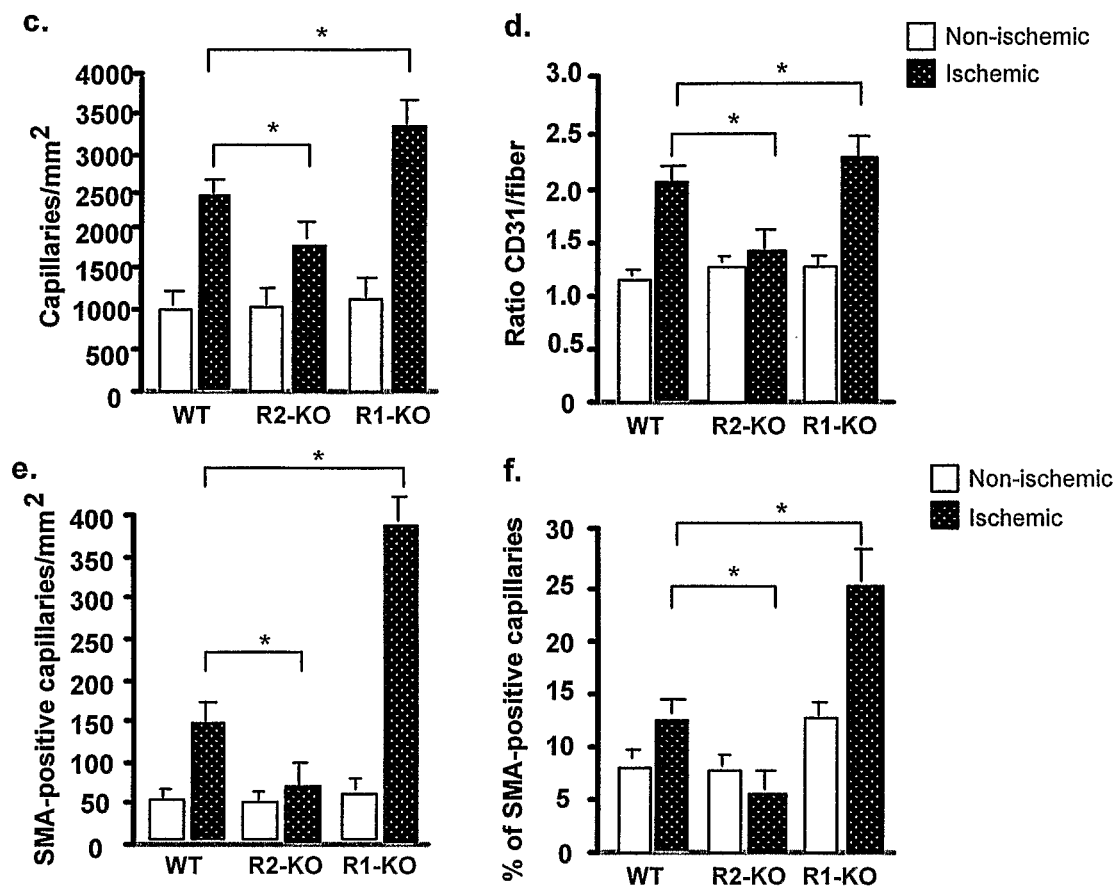

FIG. 9 shows quantitation of capillaries (number/mm2 muscle area) (top left), ratio of CD31/muscle fiber (top right), SMA-positive staining (number/mm2 muscle area) (bottom left) and % of SMA-positive staining (SMA/capillaries) (bottom right) in gastrocnemius muscles harvested as shown, 4 weeks after femoral ligation. Data from different mice are shown in graphics and n=4 for each strain. *, p<0.05.

Figure 10:
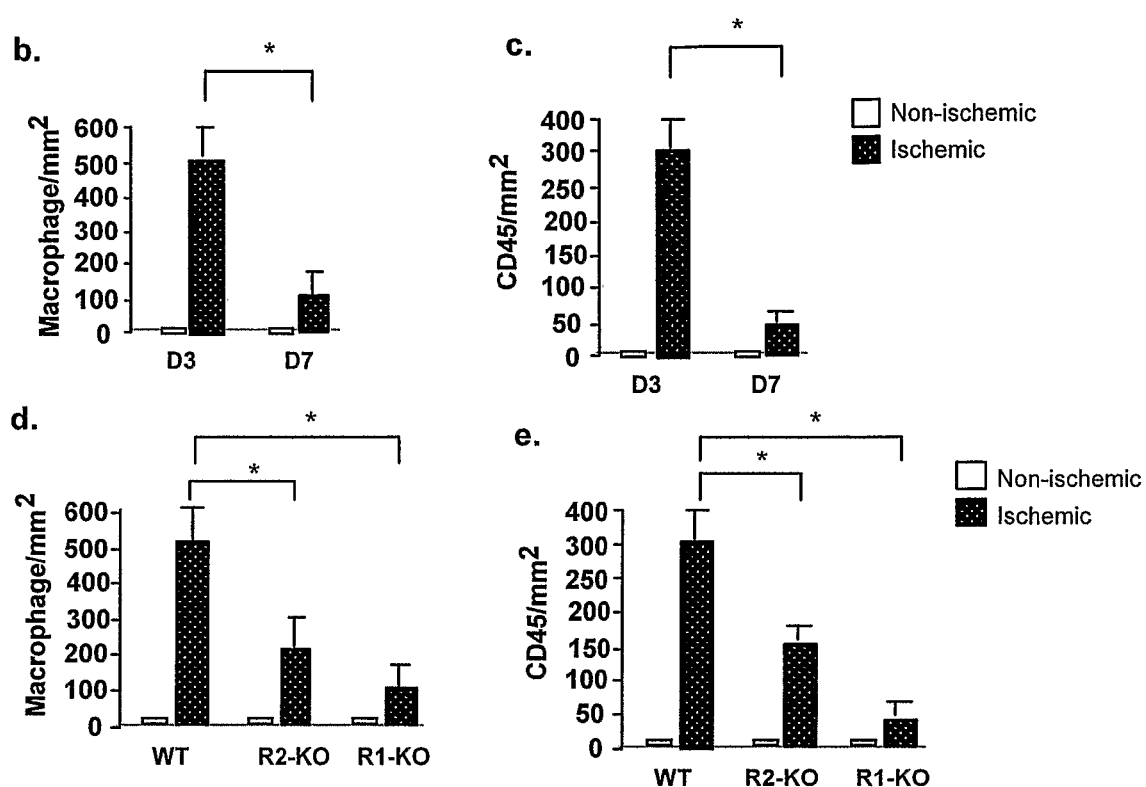

FIG. 10 shows the infiltration of immune cells, tissue necrosis/apoptosis and cellular proliferation in TNFR1-KO and TNFR2-KO mice in response to ischemia. F4/80- and CD3-positive cells from non- and ischemic hindlimbs in C57BL/6, TNFR1-KO and TNFR2-KO mice on day 3 post-ischemic were counted as number of infiltration/mm2 muscle area, as shown.

Figure 11:
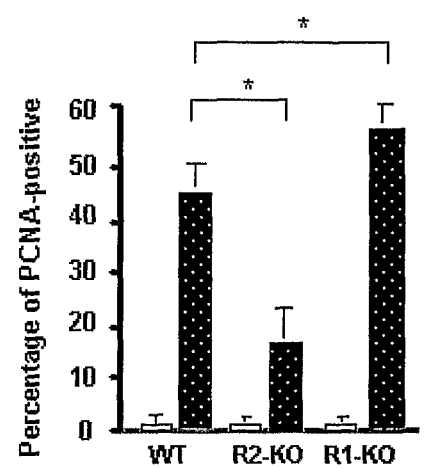

FIG. 11 shows the percentage of PCNA-positive cells were counted as number/mm2 muscle area in C57BL/6, TNFR1-KO and TNFR2-KO mice on day 3 post-ischemic. Data from different mice groups are shown in graphics and n=4 for each strain. *, p<0.05.

Figure 12:
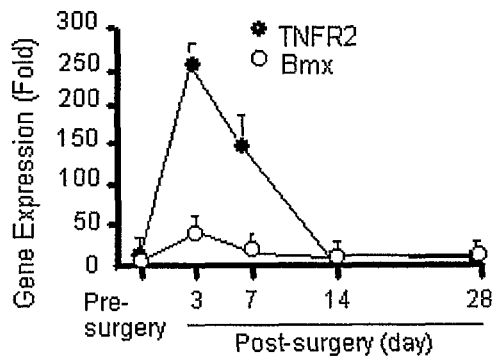

FIG. 12 shows gene expression of TNF, TNFR1, TNFR2, TRAF2 and Bmx as determined by qRT-PCR. in C57BL/6 (n=3) mice subjected to hind-limb ischemia. Hindlimbs were harvested on day 0, 3, 14 and 28 post-surgery as indicated. 18S rRNA was used for normalization. Induction fold (left/right) is shown.

Figure 13:
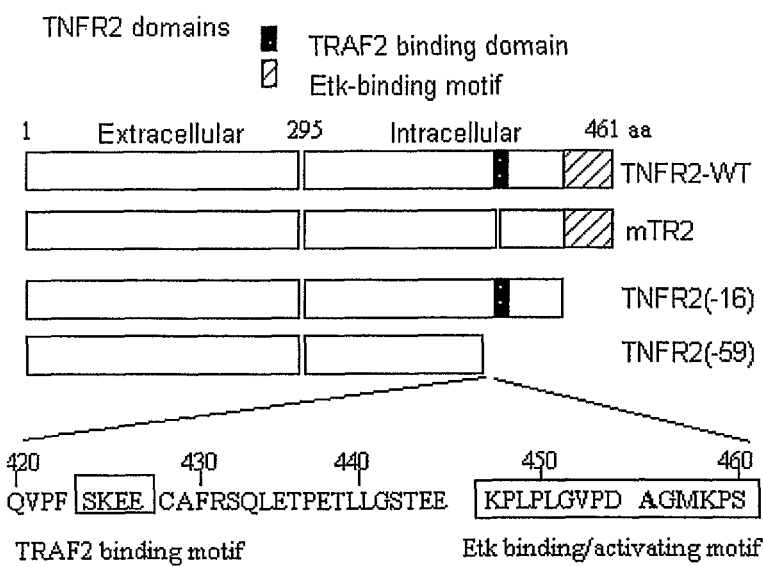

FIG. 13 shows schematic structure for TNFR2. The numbers refer to amino acid number indicating the boundary of the extracellular and intracellular domains. TRAF2- and Bmx/Etk-binding motifs are indicated. The illustrated sequence (SEQ ID NO: 2) is a part of INFR2.

Figure 14:
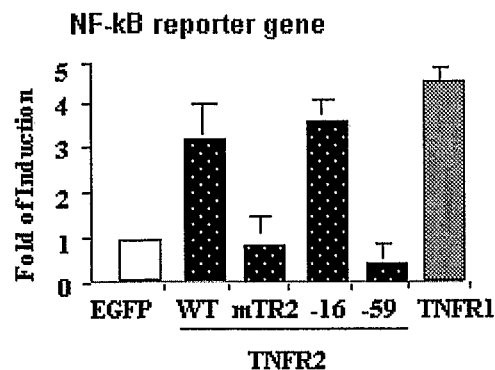

FIG. 14 shows that expression of TNFR2-WT and TNFR2(-16), but not mTR2 (mutation at the TRAF2-binidng motif) or TNFR2(-59) (deletion of both Bmx/Etk- and TRAF2-binidng motifs), activates NF-κB reporter gene. TNFR2-null MLMEC were transfected with 1 µg of NF-κB-dependent reporter gene, a β-galactosidase constitutive expression vector (0.5 µg) followed by infection with various TNFR2 retroviral constructs (1:100 MOI). Data are presented from mean of duplicate samples.

Figure 15:
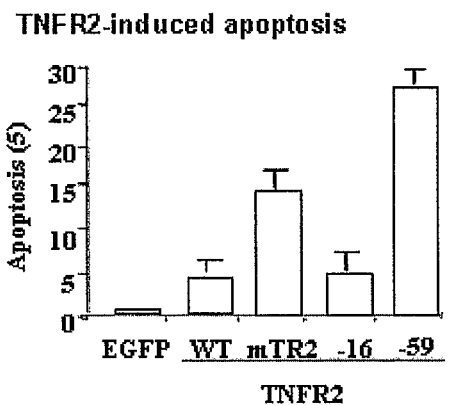

FIG. 15 shows that TRAF2-binding site is critical for TNFR2-induced EC survival. BAEC were infected with retrovirus expressing GFP or various Myc-tagged TNFR2 mutants, and TNFR2 expression was determined by indirect fluorescence microscopy with anti-Myc. EC apoptosis was determined by nuclear condensation and DAPI staining and quantitated.

Figure 16:
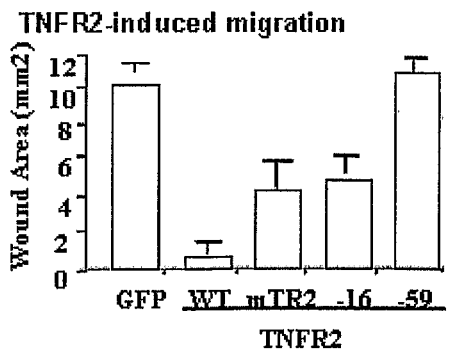

FIG. 16 shows that TRAF2 and Etk cooperatively mediate TNFR2-induced EC migration. MLMEC were infected with retrovirus expressing EGFP (VC) or various TNFR2 proteins. EC migration was performed as described previously {Pan, 2002 #1368}. Briefly, MLMEC were cultured in 0.5% FBS for overnight and subjected to "wound injury" with a yellow tip. Cells were washed with PBS once and fresh media (0.5% FBS) were added. Cells were further cultured for indicated time. The EC migration in culture was determined by measuring "wound" areas in cell monolayers. Three different images from each well along the wound were captured by a digital camera under a microscope (4×) and a haemocytometer (1 mm2/grid) was used as a standard. Wound area (mm2) was measured and analyzed by NIH Image 1.60. Statistical analyses were performed with StatView 4.0 package (ABACUS Concepts). Data presented are means (SEM) of the two triplicates from two independent experiments. Differences were analyzed by unpaired 2-tailed Student t test. Values of $p<0.05$ were taken as significant.

Figure 17:
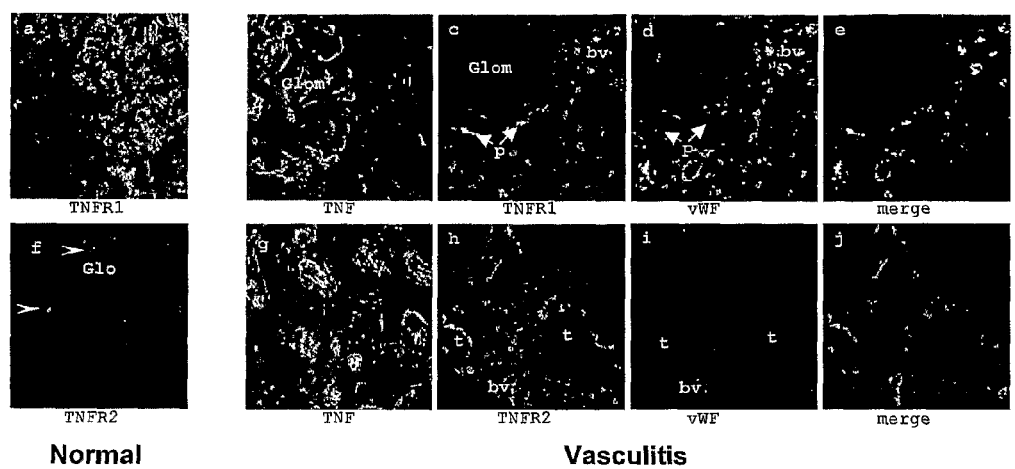

FIG. 17 shows expression of TNFR1 in glomerular endothelial cells in normal kidney (a), whereas TNFR2 is confined to isolated glomerular cells (f). Renal biopsy from patient with systemic vasculitis shows intense immunostaining for TNF (FITC) in glomerular EC (b) and tubular epithelial cells (g). TNFR1 (c=anti-TNFR1 FITC) is expressed on EC of some peritubular capillaries and small blood vessels, but not glomerular EC (d=anti-vWF Texas red and e=merged image). TNFR2 (h=anti-TNFR2 FITC) is expressed on tubular epithelial cells and some EC of small blood vessels (i=anti-vWF Texas red and j=merged image). Nuclei counterstained blue with DAPI. Glom, glomeruli; pc, peritubular capillary; bv, blood vessel; t, tubule.

Figure 18:
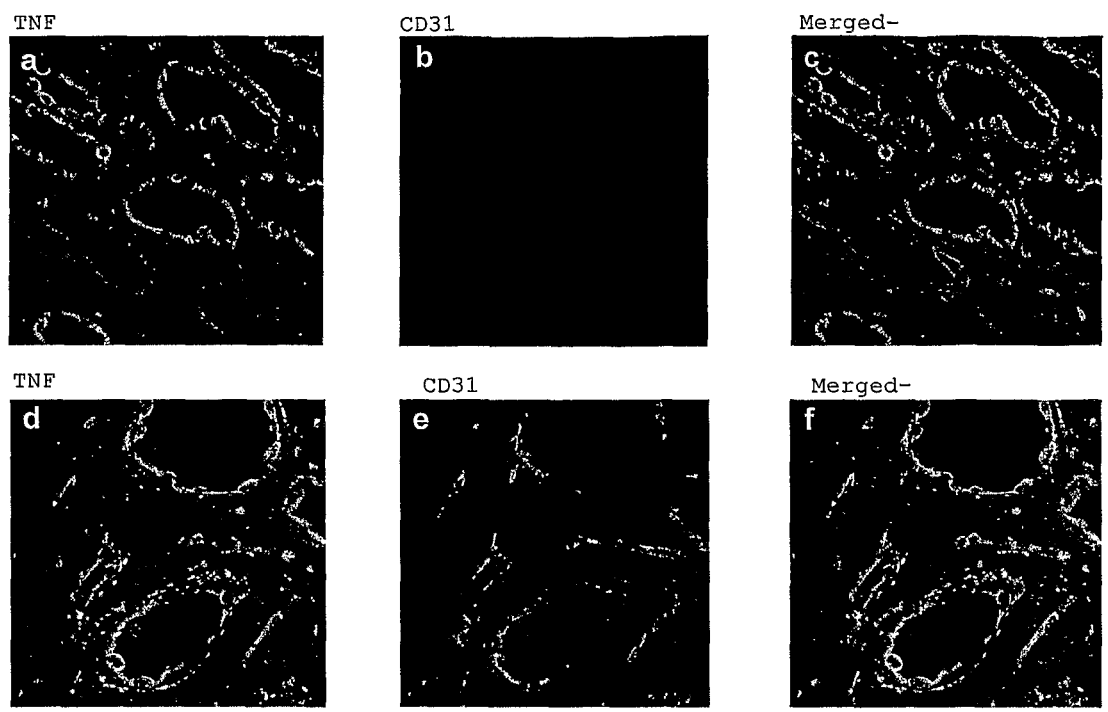

FIG. 18 shows that TNF is expressed in renal cell carcinoma. TNF is found in both tubular epithelial cells (a), which are negative for CD31, and blood vessel endothelial cells (d), which are positive for CD31 (e).

Figure 19:
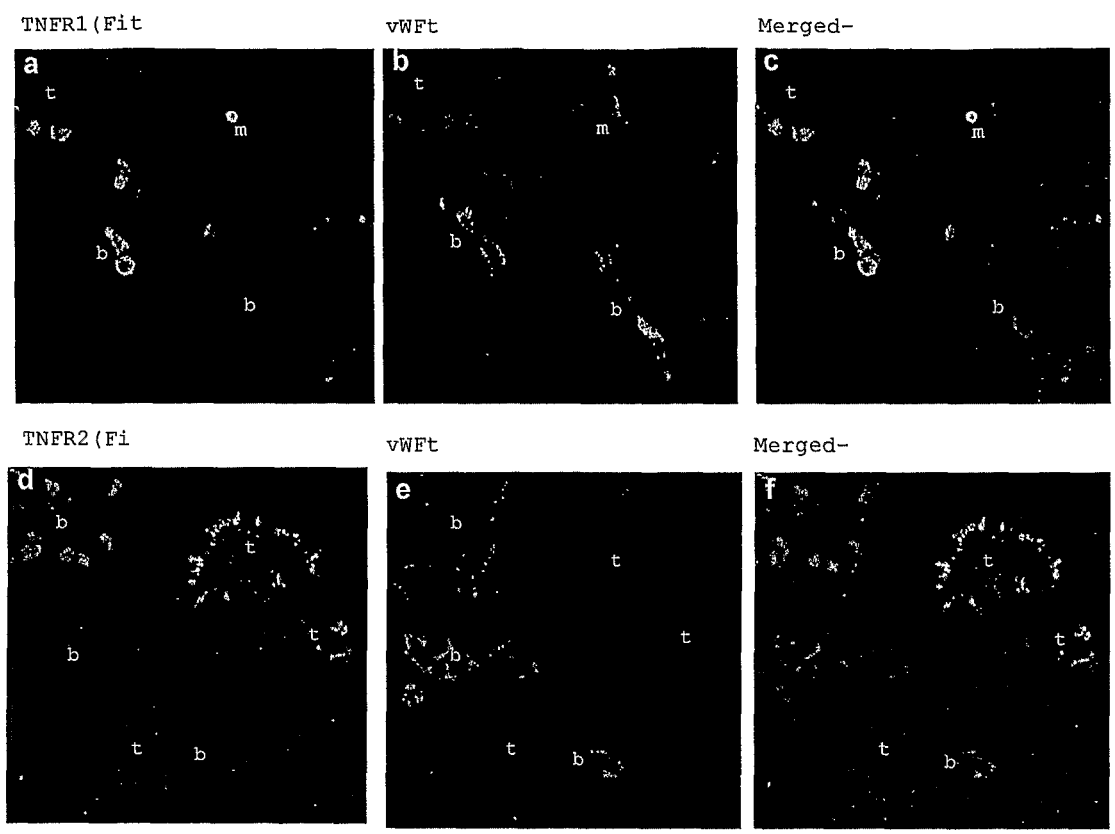

FIG. 19 shows that TNFR1 and TNFR2 are expressed at distinct sites in renal cell carcinoma. TNFR1 (a=anti-TNFR1 FITC) is expressed on endothelial cells of some blood vessels (bv), tubular (t) cells and mononuclear cells (m). Blood vessel endothelial cells are identified in b (b=anti von Willebrand factor (vWF) Texas Red). TNFR2 (d=anti-TNFR2 FITC) is expressed on some tubular (t) epithelial cells and some blood vessel endothelial cells (e=anti-vWF Texas red). Nuclei counterstained blue with DAPI. bv, blood vessel; t, tubule.

Figure 20:
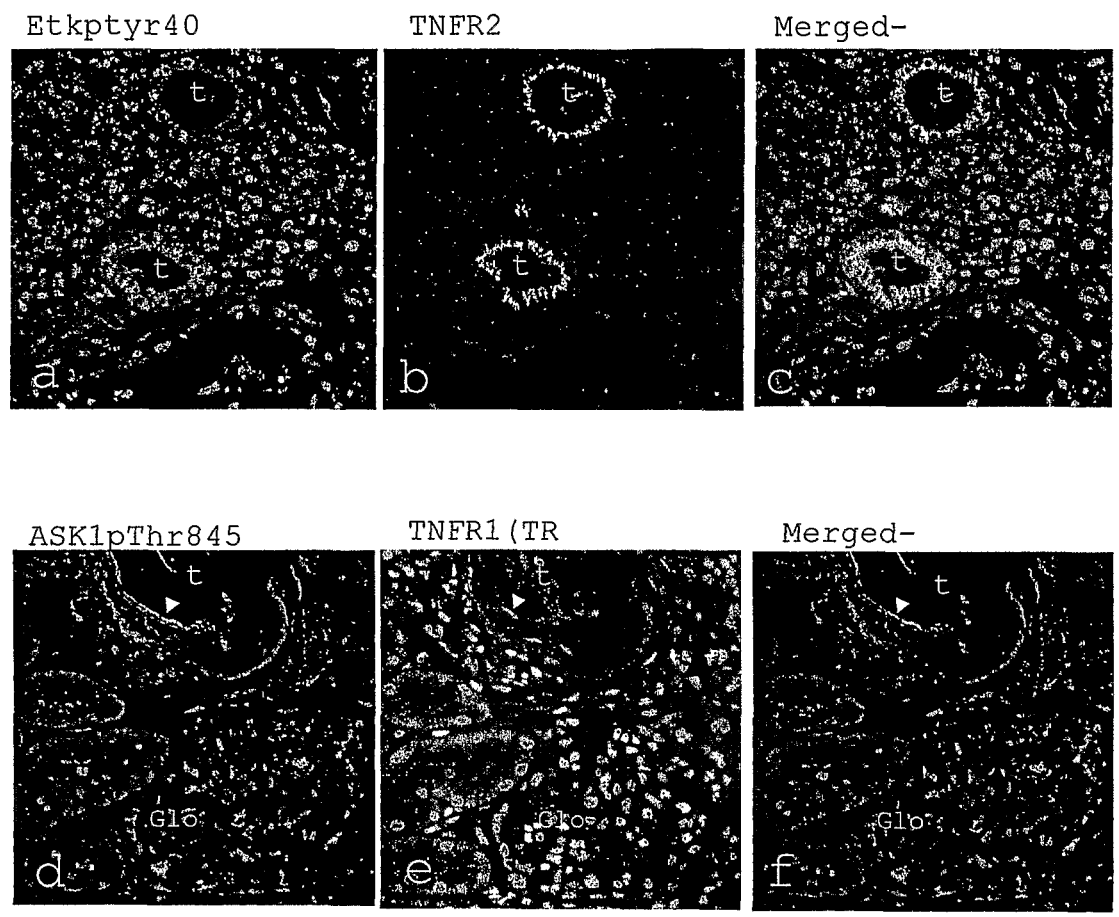

FIG. 20 shows that active forms of ASK1 and Etk can be detected by immunolabeling in renal cell carcinoma. Active Etk (a=Etkptyr40 FITC) is expressed on tubular (t) cells in renal cell carcinoma, where it co-localises with TNFR2 (b=anti-TNFR2 FITC). Active ASK1 (d=ASK1pThr845 FITC) is expressed on some tubular (t) epithelial cells where it co-localises with TNFR1 (arrowhead) (e=anti-TNFR1 Texas red). Nuclei counterstained blue with DAPI. t, tubule.

Figure 21:
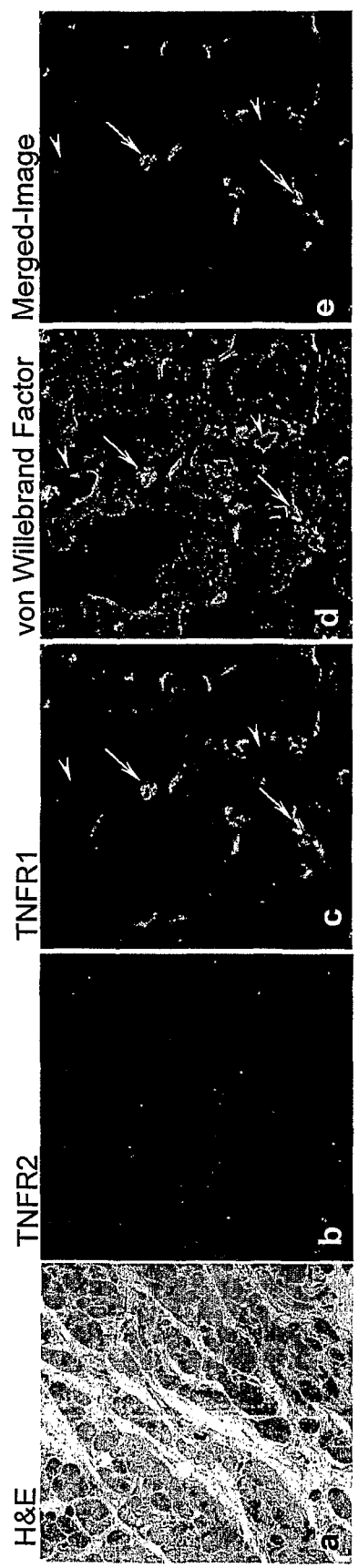

FIG. 21 shows histologically normal cardiac tissue taken at routine biopsy following cardiac transplantation (a), shows no signal for TNFR2 following immunolabeling with anti-TNFR2-FITC (b). On double immunolabeling with mouse anti-TNFR1-FITC (c) and rabbit anti-von Willebrand Factor-Texas Red (d) the merged image (e) shows that TNFR1 present in some EC of microvessels (arrows), but absent in others (arrowheads).

Figure 22:

FIG. 22 shows immunolabeling of tissue from cardiac allograft showing evidence of acute cellular rejection (a), shows no signal for TNFR1 following immunolabeling with anti-TNFR1-FITC (b). Double immuno-labelling with mouse anti-TNFR2-FITC (c) and rabbit anti-von Willebrand Factor-Texas Red (d) shows that TNFR2 is present in some EC of microvessels (arrows) in the merged image (e).

Figure 23:
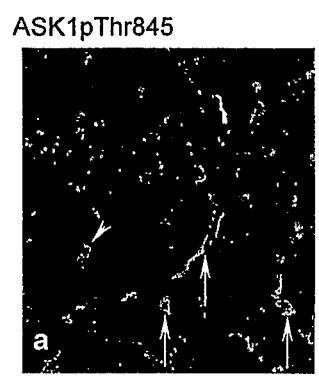
Figure 23:
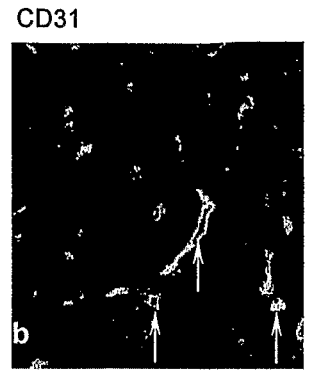
Figure 23:
Figure 23:
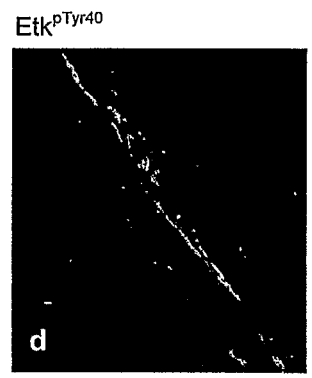
Figure 23:
Figure 23:
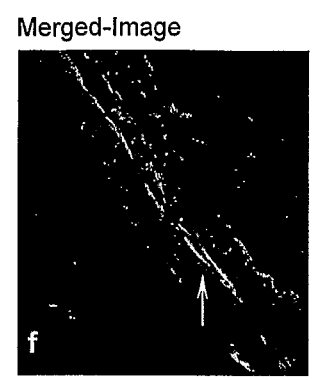

FIG. 23 shows that immunolabeling of tissue from rejecting cardiac allografts with anti-ASK1pSer967 was negative, but double immunolabeling with rabbit anti-ASK1pThr845-Texas Red (a) and mouse anti-CD31-FITC (b) reveals ASK1pThr845 on EC of some microvessels (arrows) and also on some cardiac myocytes (arrowheads), which are negative for CD31 (merged image c). Double labelling with goat anti-EtkpTyr40 (d) and mouse anti-CD31-FITC (e) shows expression on arterial EC (arrow) in the merged image (f).

MATERIALS AND METHODS

Kidney Organ Cultures

All experiments using human tissue were performed with the written, informed consent of patients and the approval of the local Ethical Committee and Addenbrooke's Hospital Tissue Bank. Renal tissue for organ culture was obtained from kidney allograft biopsies taken immediately after reperfusion of renal transplants (time zero biopsy) or from the uninvolved pole of kidney excised because of renal tumors. Duplicate 1 mm$^3$ fragments were placed in corning flat-bottomed 96-well tissue culture plates (Appleton Woods Limited, Selly Oak, Birmingham, UK), and immediately immersed in medium 199 (Flow, Irvine, Scotland, U.K) containing 10% heat-inactivated fetal calf serum (TCS, Botolph Claydon, Bucks, U.K), and 2.2 mM glutamine. Tissue was incubated for 3 h at 37° C. with either culture media alone without TNF or with 10 ng/ml of wild-type TNF (AMS Biotechnology (Europe) Ltd, Abingdon Oxon, United Kingdom), or 10 ng/ml of recombinant mutations of the wild-type TNF sequence, which enable the mutated protein ('mutein') to bind selectively to either of the TNFR subtypes (Van Ostade. et al (1993) *Nature* 361:266-269, Van Ostade. et al (1994) *Eur. J. Biochem.* 220:771-779).

The specific double mutation of R32W, S86T (here termed R1-TNF) allows selective activation of TNFR1, whereas the D143N, A145R (termed R2-TNF) double mutation allows selective activation of the TNFR2 subtype only. Half of the harvested tissue was cryoprotected in 30% sucrose in 0.1M phosphate buffer and snap frozen in isopentane-cooled in liquid nitrogen and half was immersed in 4% paraformaldehye in 0.1M PIPES buffer pH 7.6 for 1.5 hours at 4° C. and processed for paraffin-wax embedding and hematoxylin and eosin (H&E) staining.

Analysis of tissue from normal kidney and renal allografts Human renal tissue was obtained from the uninvolved pole of 9 nephrectomy specimens removed for renal tumours, and 12 different renal allograft biopsies with acute cellular rejection with or without acute tubular necrosis (ATN), or biopsies with ATN but no rejection. Cores of tissues taken from the cortex through to the medulla were divided into three portions. One portion was fixed by immersion in 2% or 4% formaldehyde (BDH Merck Ltd, Lutterworth, Leics, UK) in 0.1 M PIPES buffer, pH 7.6 for 4 hours at 4° C. for light microscopy studies. A second portion was fixed for 1.5 hours at 4° C. for electron microscopy studies. The third portion was snap-frozen in isopentane-cooled in liquid nitrogen and stored at −70° C. for immunohistochemical studies. Tissue selected for light microscopy was either encapsulated in CRYO-M-BED embedding compound (Bright Instrument Co Ltd, Huntingdon, Cambridgeshire, England) or frozen, or paraffin wax embedded. Paraffin sections from each batch of tissue were stained with H&E and classified as normal with no pathological changes, or as acute cellular rejection with or without ATN.

Light Microscopy

Single Immunolabeling

8 μm-thick cryosections from kidney organ cultures and, from normal kidney and renal and cardiac allografts, and renal cancer and renal vasculitis were permeabilized in cold methanol at −20° C. for 5 minutes, washed in Milli-Q water and rinsed in 0.1 M Tris-HCl buffer pH 7.5 containing 0.01%

TWEEN-20 (TBS) prior to incubation with blocking buffer [containing 10% fetal calf serum in TBS] (Sigma-Aldrich Company Ltd, Fancy Road, Poole, Dorset, England) for 10 minutes. Excess fluid was removed and sections were incubated with primary antibodies at 4° C. overnight, all at 1:100 dilution in blocking buffer; rabbit polyclonal raised against ASK1 phosporylated at Ser967 (anti-ASK1pSer-967; Cat #3764; Cell Signaling, New England BioLabs (UK) Ltd, Wilbury way, Hitchin, Hertfordshire, UK), rabbit polyclonal raised against ASK1 phosphorylated at Thr845 (anti-ASK1pThr845; Cat no:#3765; Cell Signaling), goat polyclonal anti-Etk (C-17; sc-8874, Bioclear UK Ltd, Mile Elm Calne, Wiltshire, UK), rabbit polyclonal anti-phospho-Etk-tyr40 (Etkp)(Cat #3211, New England Biolabs UK Ltd, Wilbury way, Hitchin, Hertfordshire, UK), mouse-anti-human CD54 (ICAM-1)(Cat # MAB2130; Chemicon International Ltd, Cardinal way, Harrow, Middlesex, UK), mouse monoclonal anti-proliferative cell nuclear antigen (PCNA)(Chemicon). Following three 5-minutes washes, the sections were incubated at room temperature in a secondary antibody diluted 1:100 in blocking buffer for 1 hour; Texas Red-conjugated goat anti-rabbit (Vector Laboratories Ltd, Bretton, Peterborough, UK) or Texas Red-conjugated rabbit anti-goat or horse anti-mouse-fluorescent isothiocynate (FITC). PCNA-stained sections were further incubated with To-PRO-3 iodide (Molecular Probes, Eugene, Oreg., USA) to detect nuclei. The sections were mounted in Vectashield Mounting Medium (Vector) and imaged with a Leica TCS-NT Confocal Laser Scanning Microscope (CLSM, Leica Microsystems, Milton Keynes, United Kingdom). For controls, the primary antibody was replaced by either non-immune serum or isotype-specific antisera and all steps were followed unchanged.

Combined Immunolabeling

Sections were incubated at 4° C. overnight with 1:100 dilution in blocking buffer of rabbit polyclonal anti-ASK1 (anti-pSer967 or anti-pThr845) and 1:500 dilution of mouse monoclonal anti-CD31 (Dakocytomation) or 1:20 dilution of mouse monoclonal anti-TNFR1 (IgG$_1$/Clone: 16803.7; R&D Systems, Oxford, UK). Some sections were incubated with either goat polyclonal anti-Etk or rabbit polyclonal anti-phospho-Etk-tyr40 and mouse monoclonal anti-TNFR2 (Cat# MAB226; IgG$_{2a}$/Clone: 22221.311 R&D systems) at 1:20 dilution or with a mouse monoclonal anti-PCNA antibody at 1:100 dilution overnight at 4° C. Following by 5-minute (×3) washes, sections were incubated for 1 hour at room temperature with 1:100 dilutions in blocking buffer of secondary antibody; Texas Red-conjugated goat anti-rabbit and FITC-conjugated horse anti-mouse or Texas Red-conjugated rabbit anti-goat or Texas Red-conjugated goat anti-rabbit and FITC-conjugated horse anti-mouse (Dakocytomation). The sections were mounted in Vectashield Mounting Media and imaged with CLSM as previously described. Controls included use of isotype-specific primary antibody or non-immune serum.

In Situ Hybridization

Non-radioactive in situ hybridisation was carried out on 5 μm-thick paraffin-wax sections of kidney organ cultures as described previously (Al Lamki, R. S. et al. (2001) *Lab Invest* 81:1503-1515). Single-stranded anti-sense DNA oligonucleotide probes 5'-end labeled with digoxigenin specific for TNFR1 (gb/M60275/HUMTNFRP, 476-515) and for TNFR2 (gb/M55994/HUMTNFR2, 844-873) (MWG-Biotech AG, UK) were used. Negative controls included incubation of sections with a sense probe to either TNFR1 & TNFR2 (MW Biotech-AG, UK).

Terminal Deoxynucleotidyl Transferase (TdT)-Mediated-Digoxigenin-11-dUTP Nick-End Labeling (TUNEL)

Apoptotic cells were detected using TUNEL method as previously described (Gavrieli, Y. et al (1992) J. Cell Biol. 119:493-501). Following dewaxing, paraffin wax sections were incubated with 50 μg/ml Proteinase-K (Roche Diagnostics), pH 7.5 for 8 minutes in room temperature. Sections were washed in Milli-Q water and exposed to TdT buffer [containing 200 mM potassium cacodylate, 25 mM Tris-HCl, 0.25 mg/ml bovine serum albumin (BSA), 5 mM cobalt chloride, pH 6.6] for 5 minutes, and incubated in a moist chamber with a mixture of TdT [0.05-0.2 U/ul] and digoxigenin-11-dUTP (Roche) in TdT buffer for 30 minutes at 37° C. Sections were then washed in TB buffer [containing 30 mM sodium citrate, 300 mM sodium chloride] for 15 minutes in room temperature, rinsed with Milli-Q water, and incubated in TBS-FCS for 10 minutes. The sections were then incubated for 1 hour with alkaline phosphatase-conjugated anti-digoxigenin-11-dUTP antibody (Roche Diagnostics). Antibody binding sites were visualized using Fast Red substrate kit (K0699, Dakocytomation) and the colour developed microscopically. All sections were counterstained with 1% aqueous methyl-green (Sigma, UK). Negative controls included omission of the TdT enzyme and, positive controls included pre-treatment of sections with 0.1 U/μl deoxynuclease-1 (DNase-1)(Roche Diagnostics) prior to TdT staining and also staining of sections of human tonsils.

Apoptotic and Proliferative Indices

The number of dead tubular cells in the cortex was counted on TUNEL stained sections from 4 different samples of kidney organ cultures from each of the 4 treatments. In a view field at a magnification of ×235, the total number of dead tubular cells was counted in at least 30 tubules/field in each sample and the apoptotic index (AI) averaged for each treatment. TUNEL-positive cells within the glomeruli were not counted. In addition PCNA-positive tubular cell nuclei was counted on 10 representative fields at a magnification of ×235 from 4 different samples from 4 different treatments. The proliferative index (PI) was calculated as a percentage of PCNA-positive tubular cell nuclei averaged for each treatment.

Statistical Analysis

Statistical significance, defined as $P<0.05$, was determined for each TNF treatment compared to no TNF treated cultures using paired student's t-test, Student's T-test, one or two-way analysis of variance followed by Bonferonni post-hoc test. All values are given as mean+/−SEM.

TNFR1-KO and TNFR2-KO Mice

Wild type C57BL/6, TNFR1-KO mice and TNFR2-KO were purchased from Jackson Laboratory (Bar Harbor, Me.). Mice were confirmed by genotyping with specific primers suggested by the Vendor. All animal studies were approved by the institutional animal care and use committees of Yale University.

Mouse Hindlimb Ischemic Model

All animal studies were approved by the institutional animal care and use committees of Yale University. 8-12 week old male congenic (F10) Bmx-KO, Bmx-SK-Tg (in house) or C57BL/6 mice (Jackson Laboratories, Bar Harbor, Me.) were used for all experiments. Mouse ischemic hindlimb model was performed as described previously (Couffinhal, T. (1998) Am J. Pathol. 152, 1667-79). Briefly, following anesthesia (79.5 mg/kg ketamine, 9.1 mg/kg; xylazine), the left femoral artery was exposed under a dissection microscope. The proximal of femoral artery and the distal portion of saphenous artery were ligated. All branches between these two sites were ligated or cauterized, and arteriectomy was performed. Sham operation is without femoral artery ligation but skin incision.

Blood Flow Measurement and Clinical Score

Blood flow was measured by PeriFlux system with Laser Doppler Perfusion Module (LDPU) unit (Perimed, Inc. North Royalton, Ohio). Deep measurement probe was placed directly on gastrocnemius muscle to ensure a deep muscle flow measurement. Ischemic and non-ischemic limb perfusion was measured pre-, post-surgery, 3 days, 2 weeks and 4 weeks after surgery. The final blood flow values were expressed as the ratio of ischemic to non-ischemic hind limb perfusion. To be more precisely evaluate the mobility of mice after limb ischemia, we designed a scoring system. 0=normal; 1=pale foot or gait abnormalities; 2=gangrenous tissue in less than half the foot without lower limb necrosis; 3=gangrenous tissue in less than half the foot with lower limb necrosis; 4=gangrenous tissue in greater than half the foot; 5=loss of half lower limb. Clinical outcome of all mice were observed and recorded at the same time points of blood flow measurement.

Microfil Perfusion 4 weeks after femoral ligation, mice were anesthetized and perfused with 20 ml of 37° C. PBS plus 10 units/ml heparin at a flow rate of 10-15 ml/min through the left ventricle. After PBS, mice received 20 ml of 4% paraformaldehyde, and 15 ml of Microfil [MV-112 (white), Flowtech, Carver, Mass.]. The Microfil polymerized overnight at 4° C., and the collagen gels and underlying abdominal musculature were harvested and clarified in graded glycerol solutions (40-100% glycerol in water, increased by 20% glycerol at 24-h intervals). The clarified specimens were viewed on an SMZ1000 dissecting microscope (Nikon).

Micro-CT Analysis 4 weeks after femoral ligation, mice were anesthetized and perfused with 20 ml of 37° C. PBS plus 10 units/ml heparin at a flow rate of 10-15 ml/min through the left ventricle. After PBS, the contrasting agent was injected followed by Micro-CT ananlyses. The vasculature was volume rendered using the 3D semi-automated image analysis approaches. In the analysis of the micro-CT images following post-mortem vascular casting we employed a contrast formulation to optimize visualization of the vasculatures. However, separation of the vasculatures from the bone based on image intensity alone remains a challenge. To further improve the separation of these structures in the automated segmentation we could decalcify the specimens as previously suggested by Duvall, C L (2004). Fortunately in our analysis of arteriogenesis/angiogenesis in the ischemic hindlimb we have a control contralateral leg for purposes of normalization.

Histology and Immunohistochemistry

Mice were sacrificed at 4 weeks post-surgery and muscles bf the lower limbs were harvested, methanol fixed and paraffin embedded. Tissue sections (5 μm thick) were stained using anti-PECAM-1 antibody (Pharmingen, San Diego, Calif.) and anti smooth muscle alpha actin (SMA) antibody (Dako, Carpinteria, Calif.). Bound primary antibodies were detected using avidin-biotin-peroxidase (NovaRed™ peroxidase substrate kit, Vector Laboratories, Burlingame, Calif.). Pictures from 4 random areas of each section, and 5 sections per mice were taken using a Kodak digital camera mounted on a light microscope (40× objective). Capillary density and SMA positivity were quantified by measuring the percentage of PECAM positive area or SMA positive area (in same area of adjacent sections) out of total area using the Matlab software (The Math Works, Inc. Natick, Mass.).

Gene Expression in Ischemic Muscle

Total RNA of lower limb muscles was isolated by using phenol/chloroform and isolated using RNeasy kit with DNase I digestion (Qiagen, Valecia, Calif.). Reverse transcription was done by standard procedure (Super Script First-Strand Synthesis System, Qiagen) using 1 μg total RNA. Quantitative real-time PCR was performed by using iQ SYBR Green Supermix on icycler Real-Time Detection System (Bio-Rad Laboratories, Inc. Hercules, Calif.). Specific primers for VEGF-A, VEGF-B, VEGF-C, Flk-1, Flt-1, Angiopoitein-1 (Ang-1), Angiopoitein-2 (Ang-2), Tie-2, PDGF-A, PDGF-B, PDGF-a receptor, PDGF-b receptor and 18S ribosomal RNA as an internal control were used. Relative amount of mRNA in C57BL/6 and eNOS (−/−) mice lower limb muscle 3 days and 2 week post-ischemia was quantified.

Renal Ischemia in TNFR1-KO and TNFR2-KO Mice

Wild type C57BL/6, TNFR1-KO mice and TNFR2-KO were purchased from Jackson Laboratory (Bar Harbor, Me.). Mice were confirmed by genotyping with specific primers suggested by the Vendor. All animal studies were approved by the institutional animal care and use committees of Yale University.

Renal ischaemia-reperfusion injury was induced by renal artery and vein clamping. Briefly, mice 6-8 weeks of age were anaesthetised with 79.5 mg/kg ketamine, 9.1 mg/kg; xylazine. Renal ischaemia was induced by clamping of the renal arteries and veins bilaterally for 30 min. After 30 minutes of ischaemia the clamps were removed and the abdomen closed. Sham treated animals underwent the same surgical procedure as the renal ischaemic mice, but without application of the clamps. Animals were killed at 24 h after renal ischaemia-reperfusion injury or sham surgery. At the time of death both kidneys were harvested for examination by microscopy. Tissue was fixed in 4% paraformaldehyde, embedded in paraffin, sectioned at 4 μm, stained with haematoxylin and eosin and examined to evaluate the degree of necrosis.

Cell Culture and Cytokines.

Human umbilical vein EC (HUVEC) from BCMM Endothelial Cell Facility (Yale University). Bovine aortic EC (BAEC) were purchased from Clonetics (San Diego, Calif.) were cultured in DMEM medium containing 10% fetal bovine serum. MLEC isolation from WT and Trx2 TG mice was performed as we described (Pan, S. et al (2002) *Mol Cell Biol* 22, 7512-7523) followed by immuno-selection and immortalization modified from the protocol described by Lim et al (Lim, Y. C. et al (2003) *Am J Pathol* 162, 1591-1601). For immuno-selection, 10 μl beads (per T-75 of mouse lung cells) were washed with 1 ml of buffer A (PBS +2% FBS) for 3 times and resuspended in 100 μl of buffer A. 10 μl (10 μg) of anti-mouse ICAM-2 or 10 μl (10 μg) of PECAM-1 were added and rocked at 4° C. for 2 hrs. Beads were washed for 3 times and resuspended in 160 μl of buffer A. Confluent mouse lung cells cultured in a T-75 flask were placed at 4oC for 5 min and incubated with the beads at 4oC for 1 hr. Cells were then washed with warm PBS and treated with 3 ml of warm Trypsin/EDTA. When cells were detached, 7 ml of growth media were added. An empty 15-ml tube in the magnetic was placed on the holder and the cell suspension (~10 ml) was added slowly by placing the pipette on the wall of the tube so that the cells pass through the magnetic field. Cells were incubated for 5 min, and the media are carefully aspirated. The 15-ml tube was removed from the magnetic holder and the beads/cells were resuspended in 10 ml of media. The selected cells were plated on 0.2% gelatin-coated flasks and cultured for 3-7 days. When the cells were confluent, another round of immunoselection was repeated. Human recombinant TNF and VEGF was from R&D Systems Inc. (Minneapolis, Minn.) and used at 10 ng/ml.

Indirect Immunofluorescence Confocal Microscopy

Fixation, permeabilization, and staining of cultured EC were performed as described previously (49). Alexa Fluor 488 (green) or 594 (red) conjugated-secondary antibodies (Molecular Probes, Eugene, Oreg.) were used. Confocal immunofluorescence microscopy was performed using an Olympus confocal microscope and acquired images were transferred to Photoshop 6.0 to generate the final figures.

Results

TNFR1 and TNFR2 Differentially Activate ASK1 and Etk at Distinct Sites in Human Kidney The effect of wild type TNF and TNF muteins on phosphorylation of ASK1 and Etk in kidney tissue in organ culture was observed. The expression of ASK1 and Etk, and their anatomical relationship to TNFR1 and TNFR2, in kidney tissue showing normal histology was characterised. A strong staining for ASK1pSer967 was demonstrated in glomerular and peritubular capillaries EC, where it co-localized with TNFR1. No co-localisation of TNFR1 and ASK1pThr845 was detected on sections of normal kidney.

Staining for TNFR2 was confined to isolated cells in glomeruli and interstitium, with a strong signal for Etk also present in glomerular EC. No co-localisation for TNFR2 and Etkp was detected in normal kidney and no immunostaining was seen when the primary antibody was replaced by non-immune serum.

Expression and Phosphorylation of ASK1 by Wild Type TNF and TNF Muteins in Kidney Organ Culture Kidney tissue maintained in culture for 3 hrs without TNF showed similar patterns of expression of ASK1, Etk and TNFRs as normal kidney. A strong co-expression of TNFR1 and ASK1-pSer967 but not of ASK1-pThr845 was demonstrated in glomerular and peritubular capillaries EC, and EC of some blood vessels were reactive for TNFR1. With the exception of a few vascular EC, ASK1pSer967 was not demonstrated on R1-TNF-treated cultures but co-localization of TNFR1 and ASK1pThr845 was observed in glomerular and peritubular capillaries EC, with weak signal for ASK1pThr845 also detected on some tubular epithelial cells. R2-TNF-treated cultures demonstrated co-localization of TNFR1 and ASK1pSer967 but not ASK1pThr845 on a few isolated cells in glomeruli and in the interstitium. Also present were some tubular epithelial cells that were weakly reactive for TNFR1. Wild type TNF-treated cultures showed moderate staining for TNFR1 in glomerular EC and peritubular capillaries, which also showed weak staining of ASK1pSer967. A strong co-localization for TNFR1 and ASK1pT845 was demonstrated in EC of glomerular and peritubular capillaries.

Expression and Phosphorylation of Etk by Wild Type TNF and TNF Muteins in Kidney Organ Culture Kidney tissue cultured without TNF demonstrated a moderate signal for TNFR2 in isolated cells within glomeruli and interstitium, with a moderate signal for Etk but not Etkp detected in glomerular EC. R1-TNF-treated cultures showed a similar pattern of TNFR2 and Etk expression to tissue cultured without TNF, with a stronger signal and co-expression of TNFR2 and Etkp seen on isolated cells in glomeruli. R2-TNF treated cultures demonstrated new expression of TNFR2 on tubular epithelial cells, where it co-localized with Etk and Etkp. Etkp was evident on some, but not all, TNFR2-expressing tubular epithelial cells. No signal for TNFR2 or Etkp was detected on glomeruli, but a weak signal was occasionally seen on vascular EC, and on interstitial mononuclear cells. A strong co-expression for TNFR2 and Etk and Etkp was also demonstrated on tubular epithelial cells in wild-type TNF treated cultures, and in mononuclear cells within glomeruli and in Bowman's capsule. Expression for ICAM-1 increased with intensity in EC of glomerular, peritubular capillaries and blood vessels, and in tubular epithelial cells in kidney organ cultures treated with wild-type TNF and R1-TNF and R2-TNF, which served as a useful internal control for tissue viability and for the detection technique.

Wild-type TNF and TNF Muteins Show Differential TNFRs Gene Expression in Kidney Organ Culture To determine whether R2-TNF and wild type TNF up regulate TNFR2 in tubular epithelial cells through new gene expression, tissues from organ cultures were analyzed for the presence of mRNA. Expression of TNFR1 mRNA but not TNFR2 mRNA was detected in glomerular EC on cultures without TNF and following R1-TNF treatment. No signal for TNFR1 or TNFR2 mRNA was detected in tubular epithelial cells or on vascular EC. In contrast, R2-TNF-treated cultures showed no signal for TNFR1 mRNA but a strong signal for TNFR2 mRNA in epithelial cells of the distal convoluted tubules and, in proximal convoluted tubules. There was no signal for TNFR1 and TNFR2 mRNA detected in glomerular on these sections. Wild-type TNF-treated cultures showed a strong signal for TNFR1 mRNA in glomerular EC and interstitial mononuclear cells and for TNFR2 mRNA in tubular epithelial cells. No mRNA signal was detected after hybridization with a sense probe to either TNFR1 or TNFR2.

Figure 2:
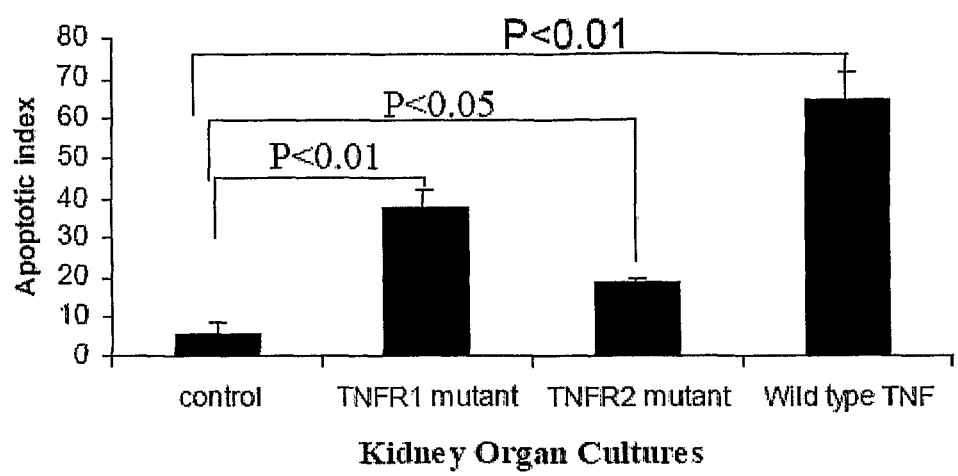
FIG. 2 shows the proportion of dead tubules in kidney organ culture treated with TNF or receptor specific TNF muteins.

Wild Type TNF and TNF Muteins cause Different Levels of Cell Death in Kidney Tissue in Organ Culture The presence of cell death in kidney tissue was examined on H&E sections and by TUNEL staining. Tissue incubated for 3 hours in culture media without TNF (control) showed normal histology with negative TUNEL reaction. Evidence of increased cell death was observed on all TNF-treated kidney organ cultures compared to controls (R1-TNF vs control $p<0.01$; R2-TNF vs control $p<0.05$; wild-type TNF versus control $p<0.01$); there was more cell death in cultures treated with R1-TNF compared to R2-TNF ($p<0.05$), and more cell death in wild type TNF treated cultures compared to R1-TNF ($p<0.05$) or R2-TNF ($p<0.01$). Apoptotic index was derived from the average number of TUNEL positive tubular cells from each of the 4 treatments and the results are summarized in FIG. 2.

Wild Type TNF and TNF Muteins Increase Expression of PCNA in Renal Cells in Kidney Organ Culture Kidney organ cultures were examined for evidence of cell proliferation using antibody to PCNA, and some sections co-localized for Etkp. Kidney organ tissue cultured without TNF and with R1-TNF demonstrated occasional PCNA-positive tubular cells, which were negative for Etkp. Wild type TNF and R2-TNF showed a strong signal for PCNA in nuclei of some tubular epithelial cells, some cells of which were reactive for Etkp. No staining for PCNA was demonstrated in glomeruli.

Figure 3:
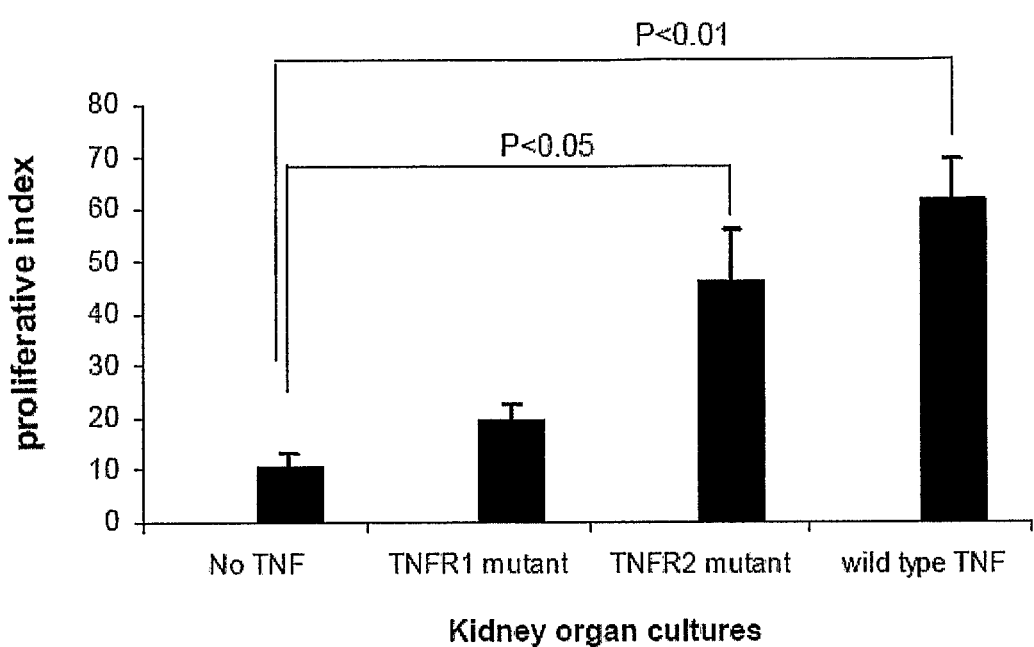
FIG. 3 shows kidney organ cultures from a times zero biopsy incubated with R2-TNF mutein for 3 hours at 37° C. A significantly high proliferative index is evident on organ cultures treated with wild-type TNF or R2-TNF compared to R1-TNF or cultures without TNF.

Proliferative index (PI) was significantly high in cultures treated with wild type TNF (63%) ($p<0.01$) and R2-TNF (50%) ($p<0.05$) but not with R1-TNF (20%) or with no TNF-treatment (10%). Calculation for the PI was based on the average percentage of PCNA-positive nuclei in tubular cells in each of the 4 treatments and the results are summarised in FIG. 3.

Expression of TNFRs, ASK1 and Etk in Renal Allografts with Rejection or ATN

Because ASK1 and Etk can be specifically activated in kidney organ culture by R1-TNF and R2-TNF, respectively, tissue from renal allografts, in which there is differential expression of TNFR1 and TNFR2 at different anatomical sites within the kidney (Al Lamki, R. S. et al. (2001) Lab Invest 81:1503-1515) was analysed. In renal allografts with evidence of acute cellular rejection, active ASK1pThr845 was strongly demonstrated in glomerular and peritubular capillaries EC and, in some tubular epithelial cells, with a strong signal for TNFR2 and Etkp observed on some tubular epithelial cells. In contrast, inactive ASK1pSer967 was not detected on these sections.

In renal allografts with ATN, there was a loss of signal for ASK1pSer967, but a strong signal for ASK1pThr845 was present on some tubular epithelial cells. In ATN, there was TNFR2 upregulation on tubular epithelial cells where it co-localized with Etkp. There were a few interstitial mononuclear cells positive for Etkp but negative for TNFR2.

In renal allografts showing evidence of rejection and ATN, ASK1pSer967 was largely absent and expression of ASK1pThr845 on glomerular EC and tubular epithelial cells was less marked than in rejection without ATN. Co-localization for Etkp and TNFR2 was also observed on tubular epithelial cells.

Figure 4:
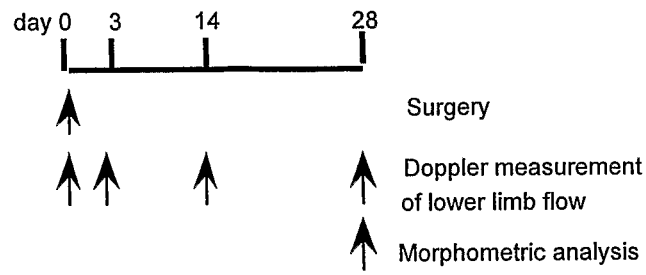
FIG. 4 shows a scheme of the ischemic hindlimb model in which blood flow of ischemic (left) and non-ischemic (right) limb were measured on gastronomic muscle at 30 min, 3 days, 2 weeks and 4 weeks after surgery by using PeriFlux system with Laser Doppler Perfusion Measurement (LDPM) unit. Tissues were harvested on day 28 for immunohistochemistry.
Figure 5:
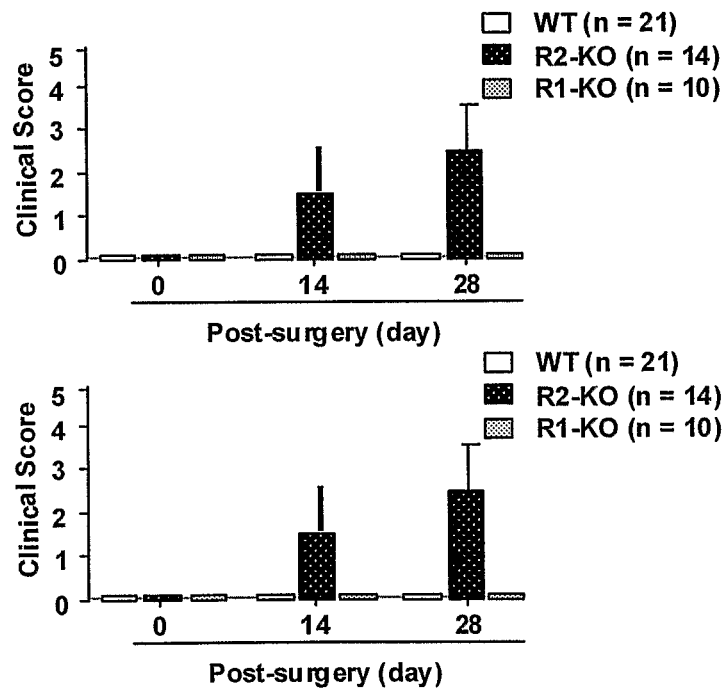
FIG. 5 shows that TNFR2-KO mice showed severe phenotype in clinical score leading to necrosis of limb. In contrast, TNFR1-KO mice, like C57BL/6, recovered completely after 4 wks.

TNFR1-KO Augments, whereas TNFR2-KO Blunts, Perfusion Recovery in the Ischemic Hindlimbs C57BL/6, TNFR1-KO and TNFR2-KO male mice were subjected to femoral artery ligation and various analyses at different time points as shown in FIG. 4. On day 14-28 post-surgery, TNFR2-KO mice showed various degrees of clinical phenotype compared to C57BL/6 and TNFR1-KO mice (FIG. 5) based on the clinical scoring system that we described recently (Bauer, P. M. et al 2005. *Proc Natl Acad Sci USA* 102:204-209). 4 out of 10 R2-KO mice had severe necrosis of the feet (FIG. 5). To precisely determine functional defects in TNFR2-KO mice, blood flow was measured and ischemic and non-ischemic limb perfusion were measured pre-, post-surgery, 3 days, 2 weeks and 4 weeks after surgery. Before surgery, the ratio of left leg to right leg gastrocnemius blood flow is 1. Post-surgery, flow dropped by 80%, and returned to a ratio of 1 over 4 weeks in C57BL/6 mice. TNFR1-KO mice showed augmented recovery of hindlimb perfusion and flow returned to normal in 2 weeks. In contrast, there was a statistically significant impairment in gastrocnemius blood flow in TNFR2-KO mice, providing indication that the impairment in blood flow in TNFR2-KO is associated with a marked increase in clinical severity (FIG. 6).

Post-Ischemic Arteriogenesis is Enhanced in TNFR1-KO Mice but is Impaired in TNFR2-KO Mice Enhanced clinical recovery and limb perfusion could be due to increased arteriogenesis from existing vessels of the upper limb or/and increased neovascularization/vessel maturation in the lower limb. We first examined ischemia-initiated arteriogenesis in C57BL/6, TNFR1-KO and TNFR2-KO mice by microfil casting to visualize vascular architecture. A reduced growth of vascular beds was observed compared to the contralateral leg in C57BL/6 mice (WT) after 2 weeks and 4 weeks of ischemia. Consistent with the flow recovery, TNFR1-KO mice showed enhanced growth of vascular beds (circled area) at both 2 and 4 weeks compared to WT mice (FIG. 7). In contrast, TNFR2-KO showed a reduced growth of vascular beds compared to WT mice (FIG. 7). Notably, the defects in vascular growth in TNFR2-KO mice resulted in tissue ischemia as evident by reddish colour in the casting tissues.

To better quantify vascular density in the upper and lower limbs of mice, we further performed 2D and 3D micro-CT with these microfil-casting samples. The vasculature was volume rendered using known 3D semi-automated image analysis techniques. Both vasculature (size>100 µM) and the bone were displayed on 3D volume. The bone was manually wiped and vasculature was quantitated by image analyses. Consistent with the image analyses for the surface vasculature, vascular density was increased in TNFR1-KO whereas was significantly reduced in TNFR2-KO mice compared to WT mice (FIG. 8). These data provide indication that TNFR1 functions as negative whereas TNFR2 acts as a positive regulator in ischemic-mediated arteriogenesis and vascular growth.

Ischemic-Induced Angiogenesis and Vessel Maturation are Enhanced in TNFR1-KO Mice but are Impaired in TNFR2-KO Mice.

Ischemia-induced angiogenesis and vessel maturation in the lower limb was characterised by immunostaining with anti-CD31 or anti-smooth muscle β-actin (SMA) antibody. After 4 weeks of ischemia, both CD31-positive capillaries surrounding the skeletal muscle fibers and SMA-positive capillaries in C57BL/6 mice were significantly increased. We further quantified ischemic-induced angiogenesis and vessel maturation by measuring capillary number/mm2 (FIG. 9 top left), ratio of capillary/fiber (FIG. 9 top right), SMA-positive capillaries/SMA-positive vessel/mm2 with quantitation of the number of capillaries/mm2 (FIG. 9 bottom left), and percentage of SMA-positive capillary (FIG. 9 bottom right). Importantly, CD31 positive capillaries surrounding the skeletal muscle fibers (neovascularization) and SMA-positive SMC (pericyte recruitment) were significantly increased in TNFR1-KO mice but reduced in TNFR2-KO mice compared to C57BL/6 secondary to ischemia (FIG. 9).

Ischemic-Induced Cellular Proliferation is Enhanced in TNFR1-KO Mice but is Impaired in TNFR2-KO Mice To determine the molecular mechanism by which TNFR1 and TNFR2 differentially regulate the ischemia-induced arteriogenesis and/or angiogenesis observed above, we examined the recruitment of inflammatory cells (primarily macrophage and lymphocytes) which have been shown be critical for inflammatory angiogenesis. Infiltration of macrophages and lymphocytes to ischemic hindlimb was determined by immunostaining with the anti-F4/80 and anti-CD3 antibodies, respectively. No macrophages were detected in non-ischemic limb. Ischemia induced a drastic increase in infiltration of macrophages which peaked at day 3 post-surgery (~500 macrophages/mm2) and declined by day 7 in C57BL/6 mice (FIG. 10 top left). Similar kinetics was observed for lymphocyte infiltration (FIG. 10 top right). We then determined infiltration of macrophage/lymphocytes in TNFR1-KO and TNFR2-KO mice, and results showed that both TNFR1-KO and TNFR2-KO mice showed significantly reduction in macrophage infiltration compared to C57BL/6 mice (FIG. 10 bottom left and right, for quantitation on day 3 post-surgery). These data provide indication that infiltrated cells to ischemic hindlimb in TNFR1-KO and TNFR2-KO mice did not account for the phenotypic differences between the two mice.

Previously, we have shown that TNFR1 mediates apoptotic/necrosis signals whereas TNFR2 mediates cellular proliferation responses in ischemic kidney models. To determine if the ischemic-induced cellular proliferative/apoptotic responses contribute to the differences in the tissue repair between TNFR1-KO and TNFR2-KO mice, we measured apoptosis by TUNEL assay and cellular proliferation by PCNA staining. Kinetics studies provided indication that apoptosis peaked at day 3 post-surgery. Ischemia-induced tissue apoptosis was dramatically decreased in TNFR1-KO mice but was increased in TNFR2-KO mice compared to WT mice. Cellular proliferation started at day 7 and sustained until 4 wks. Both capillaries and myocytes showed PCNA-positive staining, consistent with the increased total numbers of capillaries and muscle fibers at 4 wks of ischemia. Notably, nuclei of the newly generated myocytes were localized in the center of cells. Importantly, both PCNA-positive EC and myocytes (FIG. 11) were significantly increased in TNFR1-KO whereas both were dramatically reduced in TNFR2-KO mice compared to WT mice. These data provide indication that TNFR1 and TNRF2-dependent cell death/survival pathways play critical roles in ischemia-mediated tissue remodeling.

TNFR2 Signaling Complexes are Highly Induced in Vascular Endothelium of Ischemic Hindlimbs.

We next examined expression of TNFR1 and TNFR2 signalling molecules in ischemic hindlimb. TNF and TNFR2 genes were significantly induced by ischemia as determined by qRT-PCR. Similarly, TNFR2-specific kinase Bmx was also strongly induced by ischemia. In contrast, expression of TNFR1 and the adaptor protein TRAF2 were not significantly altered (FIG. 12). We next examined TNFR2 protein and TNFR2 signaling complexes by Western blot with respective antibodies. TNFR2 and Bmx/Etk were drastically upregulated on day 3 in ischemic compared to non-ischemic muscle in C57BL/6 mice. Similarly, activation of Bmx/Etk as determined by a phospho-specific antibody (pY40) was greatly induced in response to ischemia. Although TRAF2 protein was not up-regulated, TNFR2-TRAF2 complex, like TNFR2-Bmx/Etk complex, was dramatically increased as determined by immunoprecipitation assays. As controls, TNFR1 mRNA and protein were not detected in TNFR1-KO mice, and TNFR1-deficiency had no significant effects on the expression of TNFR2, TRAF2 and Bmx/Etk. Similarly, TNFR2 mRNA and protein as well as TNFR2-TRAF2 complex were not detected in TNFR2-KO mice. Bmx/Etk activation (phosphorylation of pY40) was significantly reduced in TNFR2-KO mice.

To determine which cell type expressed TNFR2, we determined TNFR2 in ischemic limb tissue by immunohistochemistry with anti-TNFR2 antibody. TNFR2 was primarily expressed in large arteries in non-ischemic hindlimbs. However, TNFR2 were highly induced in vascular endothelium including capillaries as shown for positive staining with anti-CD31 antibody. As a control, TNFR2 expression was not detected in TNFR2-KO. Interestingly, Bmx/Etk showed a similar pattern of staining. These data provide indication that activation of TNFR2 signaling in ischemic vasculature plays a critical role in ischemia-induced responses.

Both TNFR2-Associated Etk and TRAF2 are Critical for TNFR2-Induced EC Survival and Migratory Signalling To understand the significance of the upregulated TNFR2 signaling (Etk and TRAF2) in arteriogenesis/angiogenesis, we examined the effect of specific activation of TNFR2 on EC survival and migration, two critical steps for angiogenesis. The availability of TNFR2-specific TNF mutein and TNFR2-null mouse EC isolated from TNFR2-KO mice (MEC) allowed us to dissect TNFR2 signaling in vitro. We first determined the effect of TNFR2 on EC survival. We first determined TNFR2 activation on EC survival/migration using the TNFR1- and TNFR2-specific TNF mutein. Human or mouse EC were treated with WT-TNF, R1-TNF or R2-TNF for indicated times, activation of NF-kB, JNK, Bmx/Etk and Akt was determined by Western blot with respective phospho-specific antibodies. Consistent with previous findings, TNF-WT and TNF-R1 induced activation of NF-kB, JNK and Akt while R2-TNF specifically induced activation of NF-kB, Bmx/Etk and Akt. We then examined EC migration in a monolayer injury assay. R1-TNF reduced while R2-TNF increased EC migration.

TRAF2 is Critical for TNFR2-Mediated Activation of NF-κB and NF-κB-Dependent Anti-Apoptotic Signaling.

We generated a retroviral system expressing EGFP or Myc tagged TNFR2-WT, TNFR2-16 lacking Etk-binding, mTR2 lacking TRAF2-binding and TNFR2-59 lacking binding for both TRAF2 and Etk (FIG. 13). FIG. 14 documents that the retroviruses could effectively transduce TNFR2-null MEC and express TNFR2 as visualized by indirect immunofluorescence microscopy with anti-Myc Ab. Next, the effects of TNFR2 on NF-κB activation was analyzed in a κB-reporter gene assay. Expression of TRAF2 was observed to activate the NF-κB reporter gene. Expression of TNFR2-WT or TNFR2-16, but not TNFR2-mTR2 or -59, induced activation of the NF-κB reporter gene. To examine the functional relevance of these mutants, we determined TNFR2-induced EC apoptosis and migration. Expression of TNFR2-WT or TNFR2-16 did not significantly induce EC death (FIG. 15). In contrast, mTR2 or -59, lacking TRAF2-binding, induced EC apoptosis as shown by nuclear fragmentation. These data provide indication that TRAF2 is critical for TNFR2-induced NF-κB and EC survival.

We then determine the effects of TNFR2 on EC migration. Expression of TNFR2-WT in MEC strongly induces EC migration compared to the control vector (EGFP). TNFR2 lacking Etk-binding (-16) or TRAF2-binding (mTR2) reduced EC migration. Deletion of both sites (TNFR2-59) diminished TNFR2-induced migration (FIG. 16). These data provide indication that both TRAF2 and Etk are critical for TNFR2-induced EC angiogenesis.

Renal Ischemia in TNFR1-KO and TNFR2-KO Mice

All sham treated mice showed normal renal histology. Renal ischaemia resulted in tubular death in wild type and all TNFR1 KO mice. In contrast, 2 out of 3 TNFR2 KO mice showed no evidence of tubular cell death following ischaemia, and one TNFR2 KO mouse showed evidence of focal infarction. These results support a protective role for TNFR2 in renal ischaemic injury. Results are summarised in table 1.

Our studies using TNF muteins in a kidney organ culture model confirm that TNFR1 and TNFR2 cause distinct cellular responses at different sites within the kidney. Treatment of normal kidney with R1-TNF results in loss of inactive ASK1pSer967 and appearance of active ASK1pThr845 in glomerular EC and peritubular capillaries. Treatment with R1-TNF causes more cell death than R2-TNF. R2-TNF upregulates TNFR2 and causes upregulation and phosphorylation of Etk in tubular epithelial cells, which is associated with increased expression of PCNA. Upregulation of TNFR2 by R2-TNF is associated with induction of mRNA for TNFR2, and downregulation of TNFR1 mRNA and protein.

The expression of TNFR-related signaling molecules in human renal allograft biopsies was characterised in the above experiments. In acute cellular rejection, TNFR1 and ASK1pSer967 are lost from glomerular EC, but staining for ASK1pThr845 is seen in these cells. TRAF2 co-localizes with TNFR1 and ASK1 in normal kidney and in rejecting allografts. The change in ASK1 phosphorylation state may be indicative of enzyme activation mediated through TNFR1, which occurs prior to the loss of TNFR1. TNFR2 is upregulated in tubular epithelial cells during allograft rejection and ATN, where it co-localizes with phosphorylated Etk. ASK1pThr845 is also found in tubular epithelial cells of rejecting and ischemic kidney. ASK1pThr845 occurs in association with Trx-1 and -2 in the presence of nitrotyrosine indicative of oxidant injury.

Expression of TNF Receptors in Normal Kidney and Renal Vasculitis

In normal kidney TNFR1 was found to be expressed on glomerular endothelial cells, whereas TNFR2 was found to be confined to isolated glomerular cells. A strong staining for ASK1pSer967 was demonstrated in glomerular and peritubular capillaries EC, where it colocalized with TNFR1. Coexpression for TNFR1 and ASK1pThr845 was not detected on sections of normal kidney. Staining for TNFR2 was confined to isolated cells in glomeruli and interstitium, with a strong signal for Etk also present in glomerular EC. TNFR2 and Etkp were not detected at other sites in normal kidney, and no signal was observed when the primary antibody was replaced by non-immune serum. Similar patterns of immunostaining were seen in 9 samples of kidney showing normal histology.

Renal biopsy from patients with systemic vasculitis showed intense immunostaining for TNF (FITC) in glomerular EC and tubular epithelial cells. TNFR1 was found to be expressed on EC of some peritubular capillaries and small blood vessels, but not glomerular EC. TNFR2 was found to be expressed on EC of tubular epithelial cells and some EC of small blood vessels. These results show that TNFR1 and TNFR2 are expressed in a regulated manner in renal vasculitis.

TNFR1 and TNFR2 Expression in Renal Cell Carcinoma

Immunostaining of tissue from renal cell carcinoma shows TNF (FIG. 18) in both tubular epithelial cells (a), which are negative for CD31, and blood vessel endothelial cells (d), which are positive for CD31 (e). FIG. 19 shows that TNFR1 and TNFR2 are expressed at distinct sites in renal cell carcinoma. TNFR1 (a=anti-TNFR1 FITC) is expressed on endothelial cells of some blood vessels (bv), tubular (t) cells and mononuclear cells (m). Blood vessel endothelial cells are identified in b (b=anti von Willebrand factor (vWF) Texas Red). TNFR2 (d=anti-TNFR2 FITC) is expressed on some tubular (t) epithelial cells and some blood vessel endothelial cells (e=anti-vWF Texas red). Nuclei counterstained blue with DAPI. bv, blood vessel; t, tubule. Both ASK1pThr845 and EtkpTyr40 can be detected by immunolabeling in renal cell carcinoma (FIG. 20). These data show that TNFR1 and TNFR2 are regulated in renal cell carcinoma, and that active forms of ASK1 and Etk can be detected.

TNFR1 and Inactive Forms of ASK1 and Etk are Expressed in Normal Cardiac Allograft Tissue.

Histologically normal cardiac tissue taken at routine biopsy following cardiac transplantation showed no signal for TNFR2 following immunolabeling with anti-TNFR2-FITC (FIG. 21). On double immunolabeling with mouse anti-TNFR1-FITC and rabbit anti-von Willebrand Factor-Texas Red, the merged image showed that TNFR1 present in some EC of microvessels, but absent in others. Double immunolabeling with rabbit anti-ASK1pSer967-Texas Red and mouse anti-CD31-FITC revealed ASK1pSer967 on EC of some microvessels and also on some cardiac myocytes, which are negative for CD31. Double immunolabeling with goat anti-Etk(Bmx) mouse anti-CD31-FITC showed expression on arterial EC in the merged image.

TNFR2 and Active Forms of ASK1 and Etk are Expressed During Cardiac Allograft Rejection.

Cardiac allografts showing evidence of acute cellular rejection showed no signal for TNFR1 following immunolabeling with anti-TNFR1-FITC (FIG. 22). Double immunolabelling with mouse anti-TNFR2-FITC and rabbit anti-von Willebrand Factor-Texas Red showed that TNFR2 is present in some EC of microvessels in the merged image. Immunolabeling with anti-ASK1pSer967 was negative, but double immunolabeling with rabbit anti-ASK1pThr845-Texas Red and mouse anti-CD31-FITC revealed ASK1pThr845 on EC of some microvessels and also on some cardiac myocytes, which are negative for CD31 (FIG. 23). Double labelling with goat anti-EtkpTyr40 and mouse anti-CD31-FITC showed expression on arterial EC in merged images.

Selective siRNA Silencing of TNFR1

The siRNA molecule ISIS121736 (GGTGGCCTTCAG-CAGGAGCT; termed 736; SEQ ID NO: 1) was evaluated for effects on cultured human EC from umbilical vein (HUVEC) or dermal microvessels (HDMEC). We found that oligofectamine-based transfection of EC with 10 nM 736 not only reduces TNF-induced expression of ICAM-1, but also blocks TNF up-regulation of other molecules, namely E-selectin (CD26E), VCAM-1 (CD106) and HLA-A,B. 736 transfection was found to act by blocking early TNF-induced signalling events, including assembly of a signalosome complex containing TNFR1 and the adaptor proteins TRADD, TRAF2 and RIP-2; activation of JNK and P38 MAP kinases and nuclear translocation of Rel A (the p65 sub-unit of NF-kB). 736 trasnfection reduced TNF responses in HUVEC, HDMEC and dermal fibroblasts but did not affect IL-1 responses. The actions of 736 were found to be delayed, requiring hours for onset. Treatment with 736 reduced the expression of mRNA encoding TNFR1 as well as TNFR1 surface expression, but not other signalosome components or TNFR2. There was no evidence of TNFR1 shedding or of cellular toxicity at the doses used. A sequence with high homology to 736 (17 of 19 bases) is present within the 3'UT of TNFR1 mRNA. In summary the 736 molecule was found to exhibit broad anti-TNF activity, through selective mRNA knockdown.

Figure 1:
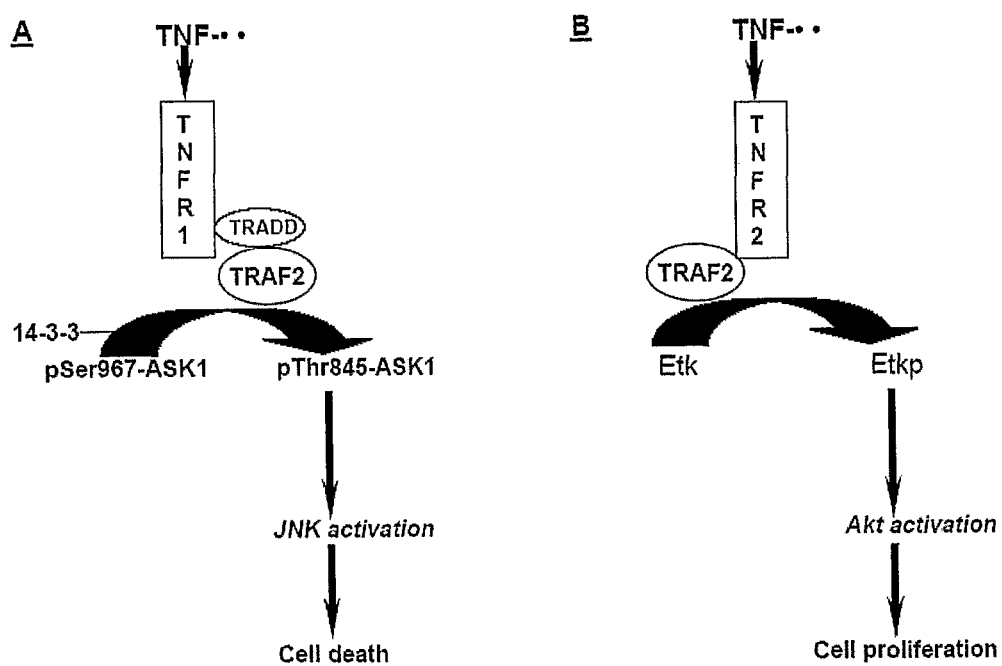

In the putative model shown in FIG. 1, normal kidney expresses TNFR1, TRAF2 Trx and inactive ASK1 and Etk. Inflammation causes cytokine production and ROS generation leading to ASK1 activation in EC and Etk activation in TEC with concomitant reduction of survival factors such as TRAF2 and Trx. ASK1 activation in EC alone appears to associate with acute rejection, whereas Etk activation by TNFR2 alone associate with ATN, which may be enhanced by increases of AIP1 and NTE. Activation of ASK1 and Etk with increases of AIP1 and NTE synergistically induce ATN and acute rejection.

TNF is shown herein to alter the phosphorylation state of ASK1 and Etk at distinct sites, for example within the kidney, leading to different pathophysiological responses. Ser967 dephosphorylation and Thr845 phosphorylation of ASK1, through TNFR1, may cause tissue injury by providing pro-inflammatory signals, and/or promote cell death. In contrast, Etk phosphorylation in ischemic injury or allograft rejection may provide an important signal for cell regeneration, for example tubular cell regeneration in the kidney, by promoting cell proliferation. In addition, the results provide for the first time, assays to determine the status of TNFR signalling in tissue samples, such as renal or vascular tissue samples.

TNFR1 and TNFR2 are also shown herein to play differential roles in ischemia-mediated arteriogenesis and angiogenesis. TNFR1 signalling inhibits while TNFR2 signalling promotes this adaptive response, due to their opposite effects on EC survival and migration. This conclusion is based on the functional analyses from genetically deficiency of TNFR1 and TNFR2 mice in a femoral artery ligation model and mechanistic studies in mouse EC isolated from these mice. Specifically, TNFR1-KO mice had enhanced whereas TNFR2-KO had reduced capacity in clinical recovery, limb perfusion and ischemic reserve capacity compared to the wild-type mice. Imaging and immunohistochemistry analyses indicated that ischemia-initiated arteriogenesis in the upper limb, angiogenesis and associated EC proliferation, neovascularization and vessel maturation in the lower limb were enhanced in TNFR1-KO whereas reduced in TNFR2-KO mice. TNFR2 proteins and signalling complexes (TNFR2-Etk and TNFR2-TRAF2) were highly upregulated in vascular endothelium in vivo in response to ischemia and in vitro cultured EC in response to hypoxia. Furthermore, mechanistic studies suggested that both Bmx/Etk-dependent EC migratory and TRAF2-dependent NF-κB survival pathways were critical for TNFR2-mediated angiogenesis. In contrast, activation of TNFR1 signalling caused inhibition of EC migration and EC apoptosis. The results herein provide indicate on that specific inhibition of TNFR1 or activation of TNFR2 signalling in EC may be a novel target for the treatment of vascular diseases such as coronary artery and peripheral arterial disease, as well as kidney and other diseases.

The mechanisms by which TNFR1 signalling inhibits whereas TNFR2 signalling promotes ischemia-induced arteriogenesis and angiogenesis are not clear. We showed that activation of TNFR1 signalling caused inhibition of EC migration and EC apoptosis. In contrast, activation of TNFR2 signalling induced EC survival/proliferation and migration leading to increased arteriogenesis/angiogenesis. These data provide indication that TNFR1 and TNFR2-mediated apoptosis vs survival/proliferative pathways in EC or/and skeletal muscle cells represent critical parallel and counterbalanced pathways in ischemia-mediated vascular remodeling. Our results showed that TNFR2 signalling is specifically activated in vascular EC in ischemic tissue. Furthermore, mechanistic studies indicated that TNFR2-associated TRAF2 and Etk cooperatively induce EC survival and migration, two components of angiogenesis. Collectively, our data strongly support the role of TNFR2 in mediating in ischemia-induced arteriogenesis and angiogenesis in vivo through multiple pathways by enhancing collateral growth, EPC mobilization and angiogenesis, resulting in enhanced recovery of blood flow and vascular remodeling. Collectively, our study suggests that specific inhibition of TNFR1 or activation of TNFR2 signalling in EC may be a novel target for the treatment of vascular diseases such as coronary artery disease and peripheral arterial disease.

TABLE 1

| Animal | Treatment | Observation |
|---|---|---|
| 1 | B6-Sham | normal histology |
| 2 | B6-ischaemia | focal infarction in the cotricomedullary junction, with extensive tubular damage. Glomeruli are well preserved. |
| 3 | TNFR1-/- Sham | normal histology |
| 4 | TNFR1-/- ischaemia | focal infarction in the corticomedullary junction |
| 5 | TNFR1-/- ischaemia | normal histology |
| 6 | TNFR1-/- ischaemia | normal histology |
| 7 | TNFR2-/- Sham | normal histology |
| 8 | TNFR2-/- ischaemia | focal infarction in the corticomedullary junction with some areas of extending to the apical cortex |
| 9 | TNFR2-/- ischaemia | focal infarction in the corticomedullary junction extending further down the medullary region, with cell death and nuclear fragments within and between tubules. Apical cortex and glomeruli well preserved |
| 10 | TNFR2-/- ischaemia | mild infarction in the corticomedullary junction. |

The invention claimed is:

1. A method of identifying and/or obtaining a compound useful in treating a disease condition selected from the group consisting of acute renal transplant rejection, acute tubular necrosis, coronary artery disease, cardiac allograft rejection, peripheral vascular/arterial disease and ischemia, comprising:

contacting a test compound with a tumor necrosis factor receptor 1 (TNFR1) polypeptide and a tumor necrosis factor receptor 2 (TNFR2) polypeptide wherein the test compound is an antibody or an antibody fragment;

determining activation of said TNFR1 and TNFR2 polypeptides, wherein the activation of said TNFR1 and TNFR2 polypeptides is determined in kidney tissue culture; and (1) identifying a test compound which activates the TNFR2 polypeptide and binds but does not activate the TNFR1 polypeptide or a test compound which binds to the TNFR1 polypeptide without activating the TNFR1 polypeptide as a compound for useful in the treatment of a disease condition selected from acute renal transplant rejection, acute tubular necrosis, coronary artery disease, cardiac allograft rejection, and peripheral vascular/arterial disease; or (2) identifying a test compound which activates the TNFR2 polypeptide and binds but does not activate the TNFR1 polypeptide as a compound useful in the treatment of ischemia.

2. A method according to claim 1, further comprising formulating the identified test compound in a pharmaceutical composition with a pharmaceutically acceptable excipient.

3. A method according to claim 1, wherein activation of the TNFR1 polypeptide is determined by measuring phosphorylation of Apoptosis Signalling Kinase-1 (ASK1) at Thr 845 and/or Ser 966.

4. A method according to claim 1, wherein activation of the TNFR1 polypeptide is determined by measuring ASK1-dependent cell apoptosis.

5. A method according to claim 1, wherein activation of the TNFR2 polypeptide is determined by measuring the level of endothelial/epithelial tyrosine kinase (Etk) and/or the phosphorylation of Etk at Tyr 566.

6. A method according to claim 1, wherein activation of the TNFR2 polypeptide is determined by measuring Etk-dependent cell angiogenesis.

7. A method of identifying and/or obtaining a compound useful in treating a disease condition selected from the group consisting of vasculitis, renal cell carcinoma and glomerulonephritis, comprising:

contacting a test compound with a TNFR1 polypeptide and a TNFR2 polypeptide wherein the test compound is an antibody or an antibody fragment;

determining activation of said TNFR1 and TNFR2 polypeptides, wherein the activation of said TNFR1 and TNFR2 polypeptides is determined in kidney tissue culture; and (1) identifying a test compound which activates the TNFR1 polypeptide and binds but does not activate the TNFR2 polypeptide or a test compound which binds to the TNFR2 polypeptide without activation of the TNFR2 polypeptide as a compound for useful in the treatment of a disease condition selected from vasculitis and renal cell carcinoma; or (2) identifying a test compound which activates the TNFR1 polypeptide and binds but does not activate the TNFR2 polypeptide as a compound useful in the treatment of glomerulonephritis.

8. A method according to claim 7, further comprising formulating the identified test compound in a pharmaceutical composition with a pharmaceutically acceptable excipient.

9. A method according to claim 7, wherein activation of the TNFR1 polypeptide is determined by measuring phosphorylation of Apoptosis Signalling Kinase-1 (ASK1) at Thr 845 and/or Ser 966.

10. A method according to claim 7, wherein activation of the TNFR1 polypeptide is determined by measuring ASK1-dependent cell apoptosis.

11. A method according to claim 7, wherein activation of the TNFR2 polypeptide is determined by measuring the level of endothelial/epithelial tyrosine kinase (Etk) and/or the phosphorylation of Etk at Tyr 566.

12. A method according to claim 7, wherein activation of the TNFR2 polypeptide is determined by measuring Etk-dependent cell angiogenesis.

* * * * *